US006825216B1

(12) United States Patent
Trail et al.

(10) Patent No.: US 6,825,216 B1
(45) Date of Patent: Nov. 30, 2004

(54) ALKALOID THAT INHIBITS BIOSYNTHESIS OF MICROTOXINS AND METHOD FOR SCREENING FOR MYCOTOXIN INHIBITORS

(75) Inventors: Frances Trail, Mason, MI (US); Raymond Hammerschmidt, East Lansing, MI (US); John E. Linz, East Lansing, MI (US)

(73) Assignee: Board of Trustees of Michigan State University, East Lansing, MI (US)

( * ) Notice: Subject to any disclaimer, the term of this patent is extended or adjusted under 35 U.S.C. 154(b) by 256 days.

(21) Appl. No.: 09/669,980

(22) Filed: Sep. 26, 2000

Related U.S. Application Data

(60) Provisional application No. 60/156,381, filed on Sep. 28, 1999.

(51) Int. Cl.[7] .................... C07D 211/16; A61K 31/4453
(52) U.S. Cl. ........................................ 514/315; 546/245
(58) Field of Search ................................ 546/245, 246; 514/315, 354

(56) References Cited

U.S. PATENT DOCUMENTS 3,219,659 A * 11/1965 Skau et al. ................. 548/966
5,942,661 A 8/1999 Keller
5,958,713 A 9/1999 Thastrup et al.

OTHER PUBLICATIONS

Hassel et al., Steric Carbonyl Protection Metalation and Cleavage of Highly Hindered Ureas, 1978, Helvetica Chimica Acta, vol. 61, pp. 2237–2240.*
RN 68579–54–4, 1–piperidine carboxamide, N,2,2,6,6–pentamethyl–N–undecyl. Reference in file REGISTRY, CAS STN database.*
Trail et al., Microbiol. 141: 755–765 (1995).
Eaton and Gallagher, Ann. Rev. Pharmacol. Toxicol. 34: 135–139 (1994).
Cotty, Plant Dis. 73: 489–492 (1989).
Cahoon et al., Proc. Natl. Acad. Sci. USA 89: 11184–11188 (1992).
Chang et al, Curr. Genet. 21: 231–233 (1992).
Trail et al., Appl. Environ. Microbiol. 60: 4078–4085 (1994).
Skory et al., Appl. Environ. Microbiol. 58: 3527–3537 (1992).
Yu et al., Appl. Environ. Microbiol. 59: 3564–3571 (1993).
Mahanti et al., Appl. Environ. Microbiol. 62: 191–195 (1996).
Chang et al., Appl. Environ. Microbiol. 59: 3273–3279 (1993).
Payne et al., Appl. Environ. Microbiol. 59: 156–162 (1993).
Keller et al., Phytopathol. 84: 483–488 (1994).
Holn et al., Molec. Plant–Microbe Interactions 5: 249–256 (1992).
Woloshuk et al., Appl. Environ. Microbiol. 60: 670–676 (1994).
Skory et al. Appl. Environ, Microbiol. 56:56: 3315–3320 (1990).

(List continued on next page.)

*Primary Examiner*—Rita Desai
*Assistant Examiner*—Janet L Coppins
(74) *Attorney, Agent, or Firm*—Ian C. McLeod

(57) ABSTRACT

The present invention provides an alkaloid compound that is an inhibitor of mycotoxin biosynthesis. The alkaloid is an alkenyl piperidine amide wherein the alkenyl is a C18 alkenyl with one or more double bonds. The alkaloid inhibits transcription of the fungus genes nor-1, tri5 and ipnA. The present invention further provides a method for identifying compounds, which inhibit biosynthesis of aflatoxin in *Aspergillus* spp. and deoxynivalenol in *Gibberella* spp. without inhibiting growth of the fungus in vitro.

2 Claims, 15 Drawing Sheets

OTHER PUBLICATIONS

Oakley et al., Gene 61: 385–399 (1987).
Trail et al., Proc. Am. Phytopathol. Soc. Nat. Mtg. Albuquerque, New Mexico 1994.
Bergh et al. in the J. Bacteriol. 178: 3908–3916 (1996).
Hikoto et al., Mycopathologia 66: 161–167 (1978).
Buchanan et al., Appl. Environ. Microbiol. 48: 306–310 (1984).
Huang et al. Phytopathol. 87: 622–627 (1997).
Russin et al. Phytopathol. 87: 529–533 (1997).
Ghosh et al. J. Stored Products Res. 32: 339–343 (1996).
Homans et al. J. Chromato., 51: 327–329 (1970).
Xu et al., Physiol. Molec. Plant Pathol. 56: 185–196 (2000).
Still et al., J. Org. Chem. 43: 2923–2925 (1978).
Peska, J., Assoc. Off. Anal. Chem. 71: 1075–1081 (1988).
Horng et al., Molec. Gen. Genet. 224: 294–296 (1990).
Arseculeratne et al. Appl. Microbiol. 18: 88–94 (1969).
Liang et al., Appl. Environ. Microbiol. 63: 1058–1065 (1997).

* cited by examiner

```
   1 tctagaacta gtggatctct gctattaagt cggtgattag cgtgctggat gcgcaatatc
  61 attagatatg cctttctttt cttttcttct ttaattttct tttgggggg ccagcacgga
 121 gatcgaattt gttggcatac catcaaatgc ctgccaccca accgcccaac tcggccagcg
 181 accaacacac cgccatatat agtgggatac gatcatgggt ctttggtggt ttcaacattt
 241 cttgagtact tttctaagcc gtgacataat gaacggatca cttagccagc acgatcaaga
 301 gaggctctct acgccatacc gggatggacc gcctgaggag acggtgtatt tggtcaccgg
 361 ggccagccga ggtacggtct atcgaatcag ggggtcctac gaaattttac tcatcaaacg
 421 caggcatcgg acgaggtctc attgaagctt ttctccaacg tcccaaaagc accgtggtcg
 481 cttggctgcg caacgtccgc accgctacgc cggcactctc ggcactaacc gtcgctgaag
 541 gcagtcggat gatcatagtg cagcttaatt ccgactcgga aactgatgcc caggcagccg
 601 tccagacatt gcgggaggag cacggggtga cgcacttgga cgtggtggtt gccaatgcgg
 661 ccatggcgac gaactttggg cccgcgtcca ccatgcccct cgagcatctc caggcgcaca
 721 tgatggtcaa catgtatgct cccgtcctac tgtttcaggc aacccgcctg atgctgcagc
 781 agtccaagca acaggccaag tttgtcttga tcggcgcccc gatcagcacc atcaccaaca
 841 tgcacgacta ctcgcgggcc ccactgacgg cgtacggagt gtcgaagctg gcggccaact
 901 acatggtgcg caagttccac tttgagaaca aatggctcac ggccttcatc atcgatccag
 961 ggtaatcaca gtccgagggt tcttgtcgca acgtatattc gctgaccgaa acatgctaga
1021 catgtgcaaa ctgatatggg cgaccaagga gcgcggctga tgggccgtcc gcaggcccca
1081 acaactgtcg cagacagtgt ggcaggcatc tgtgctcggg tatgaccatt gccttcttct
1141 ttgcgcgcgc agggagcgac gtggctaac gttggggtgg tagattgatg aagcgaccaa
1201 ggagactaca tcggggcact tcgttatcca cacggatgga tctcaactcc cctggtagga
1261 cgctagtgac gacgaagcgc agtcatatgt ttctgagacg agcagaaacg tgctggcgtg
1321 gagctggtcc agaaaggcgc ggtgaggtcc tgggttcgtg tcgcggcggc tttcgctcga
1381 tcagttcgtg tatgaccttt tcggtctttt ccgttccgtc tgtttaggct ctcacaagat
1441 aaaaccaaat tgaaacctaa cgttcgtttt catggacccc tgatggaaat atcgataccg
1501 tcg
```

FIGURE 8

```
   1 gaattcactt ctaaatgata caagcgcgaa tatctccgat taagcccacg ttaagagtat
  61 tttccaagac atgcagggac agatacagac ttccctcaag gttagaatca acgaaaggtt
 121 ccctaggcga ccagtgagag attggctttg gatagaggca gaggcagagc aacatcccag
 181 gtacacgaag ccaaccgttt tcgttcatta ttttgttttt ggtgtgattg gtccagagcc
 241 tgctcctatt ctcagcttcc tatgctttca gcctgccata aacaagatgt attactgcat
 301 agaagtttta ggctcgccgc ccgatgagct actggtcttc agatattcgg tctccgagga
 361 aagatttgtt tggtggccaa ccatccatag ctgcgtatat atgtactaca tgcccgttcc
 421 cctgggtcac cgttttcaca gaactacaca tcattttgcc tccacaaaat ctctaccata
 481 cacgatcccg tcagcatgtc ggataatcac cgtttagatg gcaaagtggc cttggtgaca
 541 ggcgccggcc gcggcatcgg tgctgccatc gccgtcgccc ttggtgagcg cggagccaaa
 601 gtcgtggtta actatgccca ctcccgcgag gccgcggaga aagtggttga acagatcaag
 661 gccaatggta ccgatgctat cgcaatccag gccgatgtcg gggatcctga ggcgacagcg
 721 aaattaatgg cggagacggt gcgccatttt ggctacctgg acatcgtgtc atcgaacgct
 781 ggaattgtat cgttcggtca cctgaaagac gtgacccag aagtatgaac cacagataac
 841 gcattcaagg catatgctaa agaaaacact aggagtttga cagggtcttc cgggtcaaca
 901 ctcgtggcca gttcttcgtg gcgcgggagg cctatcgcca tatgcgggaa ggaggccgga
 961 ttatcctgac cagctctaac accgcttgcg tcaaggggt acccaaacat gctgtatact
1021 ccggttccaa gggggctatt gacaccttg ttcgctgcat ggccattgac tgcggagaca
1081 agaaaatcac cgtgaatgcg gtggctcctg gagccatcaa gactgatatg tttttggctg
1141 tgtcgcggga gtatatcccc aatggtgaga ctttcaccga tgagcaggta gacgaggtca
1201 gctttccccc cataaactgc gtcttgttgg gttcccgctt aacgaagtct tatctagtgt
1261 gccgcttggc tctctccttt gaaccgcgtg ggcctccctg tggatgtcgc ccgggtagtg
1321 agcttcctgg catctgacac agccgaatgg gtaagtggaa agatcattgg ggtggatggt
1381 ggcgcttttc gataaacctt taccgctata tactcgtggg tgaagtgtat tctctcgtat
1441 tataaagagc tagacgtcgt atttgatagg atttgctagt taaactacaa cgtaatataa
1501 gctctactgc tcccaggtag cggggaaaaa gaccttgtat atatgcttga aaacctttca
1561 cattacacta atcacggtaa cttcatatat ccaatgcggc cgttgtgagg tggacaattc
1621 gcagttcatt gcgtcgtttt tctcacttca ccaagcacca ccgctctcat tttggaccga
1681 tctgtgaatc tatcctcgtc ctccgccacc tccgtagtcg acataacagg acaaattgtt
1741 gaaatgcgcg ttcgctctca aagct
```

FIGURE 9

```
   1 gccccataaa catggcacta ccgagcaaag ccgcccttgt gggccttgca aacacacttt
  61 cagagcaggt aaagcgttat ctggccacgg caggtgagac gaagagcccc gaagaccata
 121 aactctgtat tgaaagtgag agaactccct cctccaacga acacgcacag gcctgggaga
 181 tcgtgcgtac ctgcgaccgc atcggctcct tggttcatgg cccggttcct tggctcctaa
 241 gcaacgcgtt gtcccatctc gatagcgcct gtctagctgc tgccacccat ctcaacctac
 301 aggatatcat tgtggacgga cctagtccga catcactcga cacaatcgtc gccgcaaccg
 361 gcgtctcaga ggatttacta cgacggattc ttcgaggatg tgcccagcgc ttcattttcg
 421 aggaggttgc ccctgaccaa tacgcccaca cggatgcctc aaagatgttg cgagtgacgg
 481 gcattcatgc cttggttgga ttctcatgtg acgaagtgat gcggtcgggt gcctcctttt
 541 ccgacttctt gcagcagacg aaaggcaaac ctccgagttg gaatgtgcct tcgcctttct
 601 cattggcatt tgatcctacc aaagggctat ttgactatta cagcactgtg gacgaggttc
 661 gtggccgccg ctttgatcta ggtatgggcg gcacggaagc cacgaagcca ctggtagagg
 721 agatgtttga tttcagcagt ctacctgagg ggagcaccgt tgtcgatgtc ggcggcggtc
 781 gtggtcatct cagccgacgg gtttcgcaaa agcatcccca cctcaggttc atcgtacagg
 841 acctgcctgc cgtcattcac ggagttgagg acactgataa agtcaccatg atggagcatg
 901 acattcgtcg ccccaaccca gtgcgtggcg ccgacgtcta tcttctccga tctattctac
 961 atgactatcc cgatgctgca tgcgtggaaa tcctctccaa catcgtcacc gccatggacc
1021 caagcaagtc gcgcatcctt ctggacgaaa tgattatgcc cgatcttttg gcgcaggatt
1081 cgcagcgctt catgaatcag atcgacatga ctgttgttct gacattgaac gggaaggaga
1141 ggtctaccaa ggagtggaat tcgcttatta cgacggtaga tggtagactg gagactgaga
1201 agatatggtg gcgcaaaggc gaggaagggt ctcactgggg cgttcaacaa ctgcgtttgc
1261 gcaagtaggg gaatgcaatg gagatatcct tgggtctgtc agaagaacgg ctgagctatg
1321 attggcgaac acccttgccc taattcgtag ggtttgattt caagacaatt agacagtcct
1381 atacgtagaa ggagttcacc aaatcaatac tttcccactt ggca
```

FIGURE 10

```
   1 ggatccaggg ctccctggag ctcacgcagg tgctaaagat ctagcttcga ggaaacaagt
  61 cttttctggg ttctcagccc gcccatgacg gactacgtta tcttgagccc gaggcatgca
 121 tgcaggcggg ccagctagct gaacattatt tgttggtctt ggtttgcttc gttaaaccga
 181 tcacgcagtt ctctggtcac ccggtttcag cctcggtacg taaacaagga acgcacagct
 241 agacaatcct tgggccaagt cagaacccct cagctggtga caggagtgta catacattta
 301 ggcctaagtg cgaggcaacg aaaagggccg gctactctcc cggagcaagc cttcaccttg
 361 tgtgttttct ttcccgcttt caattgagaa ttcctgaatt ccttcctcac ctccacgatg
 421 gttgaccata tctcccccg ggcatctccc ggaccgatcc gttcctccca gactcgccgc
 481 gcccgaaagc tccgggatag ctgtacgagt tgtgccagtt caaaagtgcg atgcaccaag
 541 gagaaaccgg cctgtgctcg gtgtatcgaa cgtggtcttg cctgtcaata catggtctcc
 601 aagcggatgg gccgcaatcc gcgcgctccc agtcccttg attcaactcg gcgaccatca
 661 gagagtcttc cttcagccgg gtcggaacag ggacttccgg cgcacaacac gtactcaacg
 721 cctcatgctc atacccaggc ccacactcat gctcattctc atccgcaacc gcatccacaa
 781 tctcatcctc aatcgaatca accaccacac gctctgccca ccccaatgg tagcagtagc
 841 gtctccgcca tcttttctca ccagagtccc ccgccactcg tggagaccca gggccttgga
 901 ggagatctgg ctggtcaggc gcaaagcacc ctgtcttccc taacagtcga ttcggaattc
 961 gggggctctt tgcagtcaat ggaacacgga aaccatgccg atttcttggc tgagtcgacg
1021 gggagtcttt tcgacgcgtt tttggaagtg ggaccccca tgatcgaccc gttcctcgag
1081 tcggccccac tgccaccgtt tcaggcgcga tattgctgct tttcgctagc actacaaaca
1141 ctgacctgcc tcttccccca cgcccgctg ggctgtcagc tgcggctgac ggacggtgag
1201 gacagttcgt gcaacctgat gacgactgat atggtcatct cggggaacaa gaaggctacc
1261 gatgcggtcc ggaagatcct cgggtgttcg tgcgcgcagg atggctactt gctgagcatg
1321 gtcgtcctta tcgttctcaa ggtgctgggg tggtatgctg cggcagcagg cacccagtgt
1381 acctcaacgg cggcggtgg agaaaccaac agtggcagct gtagcaacag tcccgccacc
1441 gtgtccagtg gctgtctgac ggaagagcgc gtgctgcacc accctagtat ggtgggcgag
1501 gattgtgtgg atgaggaaga ccagccgcga gtgcgcgaca gcttgttctg agcgaactgc
1561 accgagtgca gtcgctggcg aacctattgg ccaagcgcct gcaagaaggt gggagacgatg
1621 cagcagggat accggcgcac catccagcgt ccccttctc actactcggt tttagtggcc
1681 tcgaagcaaa tctccgccac cgcttgcgcg ccgtgtcctc cgacattatc gattacctgc
1741 atcgagaatg aagaaaagcc ccaccgccag agcagatgac aggcctgttt ccctctccat
1801 tgagattgga atgatatcga catgatatca gctcacccgc tgcccctcac ccccttgcga
1861 ttagtgtttt tgcgcctttt tgggtgcagg gggggagcaa atcgtggcaa ccgccatctc
1921 gccaggatcc gtctttgtca tggttacatt gcatccacga tttctcttcg atcaaccggc
1981 cttgaaaggg cgagactggc cgatcgatca acacacgcgc tccagtggcg attacgatgc
2041 acggatcatg caacttttac aaattcatcg cccgtgtagg tttcaattct ggattgagcg
2101 atcatcattg ctccccacaa gaagcagggt gaagagtcgt tggtgttggt ggaacgtgtt
2161 gttgcttgtt agggccctac gaatgcagaa caagccctaa gccctgagag cgctcggatc
2221 aggtggggtc ccgtgatccg tccaacgaaa tgatcgaaaa taaccgaccc gttgtaatga
2281 tcaagaattc aatgattccc tgtaaaccct caaattgctt ggagtgaaat ttctatatag
2341 aatactaata atacgaatct tgaacagtct atacaatcta tacgtgtaa ttagttaaat
2401 tttccttata gctaaagata gagtaatagt aaattatacg ttgaaaacag aaatatatat
2461 tttttagttc cgggtctgtt atccggatca gattttaaaa ttcaaaaatc ctaaaaaaaa
2521 atagtaagca tataatatta gaatcatata tgtttgacat tactagggtc agcatgatcc
2581 actctattct cctataagcc attcggtatg atcagatgct cgaaattggt ctcggactcc
2641 ggtgacagga cccgatagga gggggggcag agcatgtgtc ggaaagcgaa aaccagaagt
2701 acgatgcaag gaattactat tcaagaagct ggattgacac ttcgggattg cccgaggatc
2761 caccttccca agataggtaa tacatacagt tgtcgatcat cttaagcgtt ggtatgctta
2821 tcttgcgtca tgatttccaa gctt
```

FIGURE 11

```
   1 atgccccaga agggagcacc gctgtaggcg caagctgacc gagttgggag cgcaaagcgt
  61 ggccgcggct gcgattgcgc tcgcatacct gcttcacaag tcgccgtacg ttttcccggt
 121 gatcgggtgc cggacggtcg agcagctgga ggcgaatata cgcctcggtg tagagctcag
 181 tgatgaggaa atgtacgaga ttgaagacac gatcccttt gatgtcggct tccccatggc
 241 gttcttattc gaatcgcccc agcagaagta ccgtagtgat atgacgacca ggcatatctg
 301 gcaggttacc tgcaatgccc ggatcgagag tgtgcctaag ccgagagtat gtatctctca
 361 acctgaattt atgatttcgc taatcgaact taccgccta tcgagccaaa gcagggtaca
 421 agcagatgga tcggaagtag ttctcggtag cattagccaa gcatcgggtc ccgagcgttc
 481 aagtatttta tatatgagcc ttgtttcctt cctatgtcat ggtagccagt atccataagg
 541 tataggaatc aaccatgtcc tcctccgata attaccgtct cgatggaaaa gtcgctctgg
 601 taactgggc tggccgcggc atcggagcag ccatcgccgt agccctcggt cagccgggcg
 661 cgaaggtcgt cgtcaactac gctaactccc gtgaggccgc agaaaaggtc gtcgacgaaa
 721 tcaagtcgaa cgctcagagc gccatttcca ttcaagccga tgtcggtgac cctgatgccg
 781 tcaccaaact gatggatcag gccgttgagc acttcggata cctggatata gtctcatcta
 841 acgcgggaat tgtctcgttc gggcatgtca aggacgttac gccagatgta tgcgtcccat
 901 ctccttacga aagtcctgta gagctctgac ctcagcagga attcgaccga gtatttcggg
 961 tcaacacgcg cggacagttt ttcgtcgccc gcgagcgta tcgccatctg cgtgaaggcg
1021 gacgcatcat cctcacaagt tccaacacag ccagcgtcaa aggcgtcccc aggcacgctg
1081 tgtactcggg ctctaagggg gcgattgaca cctttgtgcg gtgcctagct atcgactgcg
1141 gcgacaagaa gatcacggtc aacgcggtcg ctccggcgc catcaagacc gatatgtttc
1201 tatccgtgtc gcgagagtat atccccaatg gggagacttt tactgatgag caggtggatg
1261 aggtacgttt gtctttgtgt ctagtatcta cggcggccgc taactggaca gtgtgccgcg
1321 tggctgtcgc cgctaaatcg ggtcggatta ccggttgacg tggcccgggt ggtcagcttt
1381 ctagcttcag atgcggccga atggatcagt ggaaagatta ttggcgttga tgggggggcc
1441 tttagataag tcacatcata tacttgaact atataggta gacatgcaat gttcgctccc
1501 cgctcgctta ccgatatctg ccgatcatcg tcagcaacca ttaggtcacg aaaaaaagag
1561 tatactaaga gtaaacatcc gtgcatggta tgaattagt tgggtacacc gcagttagtc
1621 acaccgtact taagtacact cagcgattca cttaggcggc tgaatcggca tttcatactc
1681 tgccagcacc ggaggcccag caacatcaac aacaataggc aaagcatgca cacgctcaaa
1741 ccaggtagat aggttgcggt gctcatccct ccagcgttta tcaaggaaaa accggaatgc
1801 gccctgcaca atcccgagca caaacagatc agctaggctg agggtttccc cgaccaagta
1861 ctctcgccca caaagatggt tgtcaagaat ctttagccgt gctaaagtgt catctttgct
1921 ttgatatatg ttgtcagcat tgaagttggc tcgtccgatg agcgggttga accagccccc
1981 taacgctggg aggattcgg tgatcccgaa ggccatccag cgaatgatgg aggcatattc
2041 ttgtccggta gtcccaagta aagtcgtatt tgaatcttga gatgttacta tacctcttag
2101 tcaggaattg aatagatgga attgcagtag cagcatggta ccatagagag caatagcaat
2161 agattccgtc aatacgtacg cgtcggcccc cacaaacgta ggaatcttgc ctagagggtt
2221 gagctggaga tactcttcgg tagcatcttt gaatgaagtg atggtcttga ttttcagagg
2281 caaattgttc gcttttgcaa tcgcaagaat cgccagcgac cgcgggttga acgggcgagt
2341 gtacagagtg ccgaacggca ttgcagaaat attctcaatt cagagctgat tctcgtattg
2401 tatgcttgtg gcaacctgct aaatacaaat actgacagca aatcaactat atgtcaagac
2461 catgcccttc agctgtccgc gtaaccctaa cttcccccag gacaacggcc ttcatctttc
2521 cccgatccgt gaaacggtcc tcgtccgcca taacttcggg gctgctcatg acggggacaa
2581 actcctcgaa ggtggcttgg ctcgcaaatt ggacaacagc aaatgcgtcg aaggtcaaat
2641 cgatcgagtc gccggccagc gggggtgaccg gttgctgcag gtagtgtcgg gtgtggctga
2701 ctggaaaggc cctcccgccg agtcgttgca gcagggggat atgttcggtc tcccagtggt
2761 tacgaaattc gctggggtgtg aggtcgccgc gacgggctac aagaatcaag acagtgaaca
2821 tggtggagtg aaagtgctgt gtatgtttgt ccacacttgc ttccagaatc tcgcgcaata
2881 cgcctctata tatgcctgt ccctattctg gtcgccgaac gaactaaaca attattcaga
2941 gagactcttc ttacattttt gtcattgttg ccaaagtcac ttcactcatt gctgtcctcc
3001 aaccatgtac acaactatca tcacagcggt atgcgtgcta ttcgctcttc acctcctgga
3061 cagcttctat caagcgcggc aggaggtatg ggccctccag cgggcaaacc tagtacgagc
3121 cctctgaccc aatgattggc tagaggacga ttaactggtg atacaagccc atgccttctt
3181 tcagcctgct gaccggccac tttggtgcca tcaaacaaac catcgatgc atgccgccca
3241 acgcaaccct gcatagcatt atgctgaaat tgtcgcaaaa gttccgctca gggatgttct
3301 acatcaacat gtggccattc agcggtacat ggctcgtggt cgcaacaccg tctggcgcgg
3361 cccagatcca gagtctgaat ctttcgaagc cgccgctggt gcgaagaccg ctggagacta
3421 tcaccggggg cccaagcttg atgagtatgc atggtgaaac atggaaacgg tggagggcac
3481 tgtttaatcc aggctttaac cccaactact tgattgggct ggcgccgctg atcgccgatg
3541 aggtcgttgt tttttgcgag cagctacggc agaaggccag aacaggaaca gttttccagc
3601 ttgaaccgct cactctgagg ttgacagttg atacgatttg ctctgtgacg ttgtatgtgg
3661 ttactcccgt tgggcgatgg ccctttctaa ccctgactt agagattcac agctccacca
3721 ccaaactcag gaccaccccc ttgcctcagc gctgcaacgg cagatcgaat gggcctcgtt
3781 tggaactacc ttcaacccct taaggcggt acctgaccgt gcggcctctg tgatgtggt
3841 acaataaccg ccttatgaac cgcttcatcg accaagaggt tgaccgagcg taccgggagc
3901 agtctggccg tcagtcgaaa tccgtgatct ccctcgccct cagagattac atgaaagaga
3961 aagatggaag tctggaagac ttcaaacgac gtgttgcgcc acagttacgg gtctttctct
4021 tcgcaggtag agatacaacg agcagtacac tgctctatgc attctacctg ctttcccgac
4081 atccagaggc cctagctaag gtgcgcttag agcacgacca ggtcttcggc ccatatcatc
4141 aacaagtaca cgagaaaatc caccaagatg cgaaactcct caaccaactc ccctacacaa
4201 cagctgtcct taaagagact ctgaggctct tccctccgtc tgcctccatg cgtgaagcgg
4261 acccggcgtt gaaatcaccg acgacaacgg ccaagtatat cccactgcag
```

FIGURE 12

```
   1 tgtacctatc gcttgcgtag ctctttacta catgtgccga gctaaagata aaatcggact
  61 aaagattcgt cccgggagcc gagctaaaga taaaatcgga ctaaagattc gtcccgggag
 121 ccgaatgcta tctcaagctc gtcgtgttgc aggggatgga agacctccag tgtacgtcac
 181 ggtctctatc actacgaatt tactgggaag gctatttgca ttaacgtcaa gttaatcatt
 241 aggcctaaca acacaagcac aactaaagat tgtggatggt tgacatttac catatgctga
 301 tatatagttg atagcaacag cactttgcaa tagaacaata atagcgattt gacttgaaaa
 361 ctcaccaaga atcgttacca attattatac cattatcatc atggagaact ttcccactga
 421 gtatttctc aacacttctg tgcgccttct cgagtacatt cgataccgag atagcaatta
 481 tacccgggaa gagcgcatcg agaatttgca ctatgcttac aacaaggctg ctcatcactt
 541 tgctcagcca cgacaacagc agctgctcaa ggtagaccct aagcgactac aggcttccct
 601 ccaaaccatt gttggcatgg tggtatacag ttgggcaaag gtctccaaag agtgtatggc
 661 ggatctatca attcattaca cgtacacact tgttttggat gacagcagcg atgatccgta
 721 tccggccatg atgaactatt tcaacgatct tcaggctgga cgagaacagg cacacccctg
 781 gtgggcgctt gtcaatgagc actttcccaa tgtccttcga cattttggtc ccttctgctc
 841 attgaaccct atccgcagca ctcttgactg taagtaccct ggctctatta tttcaccacc
 901 ccaataagct aacagtgatg gaattgcagt ttttgaggga tgctggatcg agcagtacaa
 961 ctttggagga tttccaggat ctcatgatta tcctcagttt cttcgacgca tgaatggctt
1021 gggccactgc gtcgggcgt ctttgtggcc caaggagcag tttgacgagc gaggtctatt
1081 ccttgaaatc acatcagcca ttgctcagat ggagaactgg atggtctggg taaatgatct
1141 tatgtcattc tacaaggagt tcgatgatga gcgtgaccag atcagtctcg tcaagaacta
1201 cgtcgtctct gatgagatca ctctccatga agctttagag aagctcaccc aggacactct
1261 acactcgtcc aagcagatgg tagctgtctt ctctgagaag gaccccagg tgatggacac
1321 gattgagtgc ttcatgcacg gctatgtcac gtggcacttg tgcgatcaca ggtaccgcct
1381 taatgagatc tacgaaaagg tcaaaggaca aaagaccgag gacgctgaga agttttgcaa
1441 gttctatgag caggctgcta atgtcggagc cgtttcgcct tcggagtggg cttatccacc
1501 tattgcgcaa ttggcaaaca ttcggaccaa ggatgtgaag gatttgaagg atgtgaagga
1561 tctgaaggag attcagaagc ctcttctgag ctcaattgag ctagtggaat gaccgacggt
1621 gagatggaag tatgttttgc gggtactcgc taggagaata ctggtcgttt atcatgatta
1681 caaatagctt ggttgtgttt ttattagcat ttacagttga acaaggataa ttcctactga
1741 ataggcagct gaaactgatg tctgtaactc cagcctgttc gttatccgct tgcctgcag
```

FIGURE 13

```
   1 cccettgacg cccgcacaac gaacaacttg acgttcctca ccgctcaact tcaaggccat
  61 ctttcctcct tctctcttct cctcttcctt ttacctactc cccgtcgact gtctcccca
 121 gtctatccaa caacccttct ccaacgacct cttcgccgtt ttcaaaccca ccttttccta
 181 ccaacaacgc caaaatcccc tccacaatgc gtgagatcgt atgttgctcc ctaccccgg
 241 tgggggaga agtctgctca aaaagcccta tcccccccc ctgataggga ccccacccgt
 301 tctccaatac tacaaggttg ctgacggagt ttgtttcatc atataggttc accttcagac
 361 cggccagtgt gtaagttcga ctatgatttg atgtctagca ggaccatggc gacggatact
 421 aaacgtatgt tggtgatagg gtaaccaaat aggtgccgct ttctggtatg tctcaatgcc
 481 ttcgagttag tatgctttgg accaaggaac tcctcaaaag catgatctcg gatgtgtcct
 541 gttatatctg ccacatgttt gctaacaact ttgcaggcaa accatctctg gcgagcacgg
 601 ccttgacggc tccggtgtgt aagtacagcc tgtatacacc tcgaacgaac gacgaccata
 661 tggcattaga agttggaatg gatctgacgg caaggatagt tacaatggct cctccgatct
 721 ccagctggag cgtatgaacg tctacttcaa cgaggtgcgt acctcaaaat ttcagcatct
 781 atgaaaacgc tttgcaactc ctgaccgctt ctccaggcca gcggaaacaa gtatgtccct
 841 cgtgccgtcc tcgttgatct tgagcctggt accatggacg ccgtccgtgc cggtcccttc
 901 ggtcagctct tccgtcccga caacttcgtt ttcggccagt ccggtgctgg taacaactgg
 961 gccaagggtc actacaccga gggtgccgaa cttgttgacc aggttgtcga tgttgtccgt
1021 cgcgaggctg agggctgcga ctgcctccag ggtttccaga ttacccactc cctcggtggt
1081 ggtaccggtg ccggtatggg tactctcctg atctccaaga tccgtgagga gttccccgac
1141 cgtatgatgg ccacctactc cgttgtcccc tcccccaagg tctccgacac cgttgttgag
1201 ccctacaacg ccactctttc cgtccaccag cttgttgagc actccgacga gaccttctgt
1261 atcgacaacg aggctctgta tgacatttgc atgcgcaccc tcaagctctc caacccctct
1321 tacggtgacc tgaaccacct ggtctctgct gtcatgtctg gcgtgaccac ctgtctccgt
1381 ttccccggtc agctcaactc tgatcttcgc aagttggccg tcaacatggt tcctttccct
1441 cgtcttcact tcttcatggt tggcttcgct cctctgacca gccgcggtgc ccactctttc
1501 cgtgccgtct ccgttcctga gttgaccag cagatgttcg accccaagaa catgatggct
1561 gcttctgact tccgtaacgg tcgttaccte acctgctctg ctatcttgtg atgtggcccc
1621 tatttctat ttgttctatc ctctgttgtt tgaaaactga cctttcgata gccgcggaaa
1681 ggtctccatg aaggaggttg aggaccagat gcgcaacatc cagagcaaga accagaccta
1741 cttcgtcgag tggatcccca acaacatcca gaccgccctg tgctccattc ctccccgtgg
1801 tctcaagatg tcctccacct tcattggaaa ctccacctcc atccaggagc tcttcaagcg
1861 tgtcggcgac cagttcactg ctatgttccg tcgcaaggct ttcttgcatt ggtacactgg
1921 tgagggtatg gacgagatgg agttcactga ggctgagagc aacatgaacg accttgtctc
1981 cgagtaccag cagtaccagg atgcctccat ctccgagggc gaggaggaat agtaaggatt
2041 cccattggcc ctgctctcgt gtatttgtgc taaccagttt gcagcctcga ggaggaggag
2101 ccccttgagc acgaggagta aatagcttcc agtcactaaa gactcggatt gatatctggc
2161 agcaataccc ttgataagtc ca
```

FIGURE 14

SEQUENCE LISTING

<160> NUMBER OF SEQ ID NOS: 8

<210> SEQ ID NO 1
<211> LENGTH: 1503
<212> TYPE: DNA
<213> ORGANISM: Aspergillus parasiticus

<400> SEQUENCE: 1
tctagaacta gtggatctct gctattaagt cggtgattag cgtgctggat gcgcaatatc 60
attagatatg ccttttcttt cttttcttct ttaattttct tttggggggg ccagcacgga 120
gatcgaattt gttggcatac catcaaatgc ctgccaccca accgcccaac tcggccagcg 180
accaacacac cgccatatat agtgggatac gatcatgggt ctttggtggt ttcaacattt 240
cttgagtact tttctaagcc gtgacataat gaacggatca cttagccagc acgatcaaga 300
gaggctctct acgccatacc gggatggacc gcctgaggag acggtgtatt tggtcaccgg 360
ggccagccga ggtacggtct atcgaatcag ggggtcctac gaaattttac tcatcaaacg 420
caggcatcgg acgaggtctc attgaagctt ttctccaacg tcccaaaagc accgtggtcg 480
cttggctgcg caacgtccgc accgctacgc cggcactctc ggcactaacc gtcgctgaag 540
gcagtcggat gatcatagtg cagcttaatt ccgactcgga aactgatgcc caggcagccg 600
tccagacatt gcgggaggag cacggggtga cgcacttgga cgtggtggtt gccaatgcgg 660
ccatggcgac gaactttggg cccgcgtcca ccatgcccct cgagcatctc caggcgcaca 720
tgatggtcaa catgtatgct cccgtcctac tgtttcaggc aacccgcctg atgctgcagc 780
agtccaagca acaggccaag tttgtcttga tcggcgcccc gatcagcacc atcaccaaca 840
tgcacgacta ctcgcgggcc ccactgacgg cgtacggagt gtcgaagctg gcggccaact 900
acatggtgcg caagttccac tttgagaaca aatggctcac ggccttcatc atcgatccag 960
ggtaatcaca gtccgagggt tcttgtcgca acgtatattc gctgaccgaa acatgctaga 1020
catgtgcaaa ctgatatggg cgaccaagga gcgcggctga tgggccgtcc gcaggcccca 1080
acaactgtcg cagacagtgt ggcaggcatc tgtgctcggg tatgaccatt gccttcttct 1140

-continued

```
ttgcgcgcgc agggagcgac gtgggctaac gttggggtgg tagattgatg aagcgaccaa    1200
ggagactaca tcggggcact tcgttatcca cacggatgga tctcaactcc cctggtagga    1260
cgctagtgac gacgaagcgc agtcatatgt ttctgagacg agcagaaacg tgctggcgtg    1320
gagctggtcc agaaaggcgc ggtgaggtcc tgggttcgtg tcgcggcggc tttcgctcga    1380
tcagttcgtg tatgaccttt tcggtctttt ccgttccgtc tgtttaggct ctcacaagat    1440
aaaaccaaat tgaaacctaa cgttcgtttt catggacccc tgatggaaat atcgataccg    1500
tcg                                                                  1503
```

<210> SEQ ID NO 2
<211> LENGTH: 1765
<212> TYPE: DNA
<213> ORGANISM: Aspergillus parasiticus

<400> SEQUENCE: 2

```
gaattcactt ctaaatgata caagcgcgaa tatctccgat taagcccacg ttaagagtat      60
tttccaagac atgcagggac agatacagac ttccctcaag gttagaatca acgaaaggtt     120
ccctaggcga ccagtgagag attggctttg gatagaggca gaggcagagc aacatcccag     180
gtacacgaag ccaaccgttt tcgttcatta ttttgttttt ggtgtgattg gtccagagcc     240
tgctcctatt ctcagcttcc tatgctttca gcctgccata aacaagatgt attactgcat     300
agaagtttta ggctcgccgc ccgatgagct actggtcttc agatattcgg tctccgagga     360
aagatttgtt tggtggccaa ccatccatag ctgcgtatat atgtactaca tgcccgttcc     420
cctgggtcac cgttttcaca gaactacaca tcattttgcc tccacaaaat ctctaccata     480
cacgatcccg tcagcatgtc ggataatcac cgtttagatg gcaaagtggc cttggtgaca     540
ggcgccggcc gcggcatcgg tgctgccatc gccgtcgccc ttggtgagcg cggagccaaa     600
gtcgtggtta actatgccca ctcccgcgag gccgcggaga agtggttga acagatcaag      660 gccaatggta ccgatgctat cgcaatccag gccgatgtcg gggatcctga ggcgacagcg     720
aaattaatgg cggagacggt gcgccatttt ggctacctgg acatcgtgtc atcgaacgct     780
ggaattgtat cgttcggtca cctgaaagac gtgaccccag agtatgaac cacagataac       840 gcattcaagg catatgctaa agaaaacact aggagtttga cagggtcttc cgggtcaaca     900
ctcgtggcca gttcttcgtg gcgcgggagg cctatcgcca tatgcgggaa ggaggccgga     960
ttatcctgac cagctctaac accgcttgcg tcaagggggt acccaaacat gctgtatact    1020
ccggttccaa gggggctatt gacacctttg ttcgctgcat ggccattgac tgcggagaca    1080
agaaaatcac cgtgaatgcg gtggctcctg gagccatcaa gactgatatg tttttggctg    1140
tgtcgcggga gtatatcccc aatggtgaga ctttcaccga tgagcaggta gacgaggtca    1200
gctttccccc cataaactgc gtcttgttgg gttcccgctt aacgaagtct tatctagtgt    1260
gccgcttggc tctctccttt gaaccgcgtg ggcctccctg tggatgtcgc ccgggtagtg    1320
agcttcctgg catctgacac agccgaatgg gtaagtggaa agatcattgg ggtggatggt    1380
ggcgcttttc gataaacctt taccgctata tactcgtggg tgaagtgtat tctctcgtat    1440
tataaagagc tagacgtcgt atttgatagg atttgctagt taaactacaa cgtaatataa    1500
gctctactgc tcccaggtag cggggaaaaa gaccttgtat atatgcttga aaacctttca    1560
cattacacta atcacggtaa cttcatatat ccaatgcggc cgttgtgagg tggacaattc    1620
gcagttcatt gcgtcgtttt tctcacttca ccaagcacca ccgctctcat tttggaccga    1680
```

-continued

| tctgtgaatc tatcctcgtc ctccgccacc tccgtagtcg acataacagg acaaattgtt | 1740 |
| gaaatgcgcg ttcgctctca aagct | 1765 |

<210> SEQ ID NO 3
<211> LENGTH: 1424
<212> TYPE: DNA
<213> ORGANISM: Aspergillus parasiticus

<400> SEQUENCE: 3

| gccccataaa catggcacta ccgagcaaag ccgcccttgt gggccttgca aacacacttt | 60 |
| cagagcaggt aaagcgttat ctggccacgg caggtgagac gaagagcccc gaagaccata | 120 |
| aactctgtat tgaaagtgag agaactccct cctccaacga acacgcacag gcctgggaga | 180 |
| tcgtgcgtac ctgcgaccgc atcggctcct tggttcatgg cccggttcct tggctcctaa | 240 |
| gcaacgcgtt gtcccatctc gatagcgcct gtctagctgc tgccacccat ctcaacctac | 300 |
| aggatatcat tgtggacgga cctagtccga catcactcga caatcgtc gccgcaaccg | 360 |
| gcgtctcaga ggatttacta cgacggattc ttcgaggatg tgcccagcgc ttcattttcg | 420 |
| aggaggttgc ccctgaccaa tacgcccaca cggatgcctc aaagatgttg cgagtgacgg | 480 |
| gcattcatgc cttggttgga ttctcatgtg acgaagtgat gcggtcgggt gcctcctttt | 540 |
| ccgacttctt gcagcagacg aaaggcaaac ctccgagttg aatgtgcct tcgccttttct | 600 |
| cattggcatt tgatcctacc aaagggctat ttgactatta cagcactgtg gacgaggttc | 660 |
| gtggccgccg ctttgatcta ggtatgggcg gcacggaagc cacgaagcca ctggtagagg | 720 |
| agatgtttga tttcagcagt ctacctgagg ggagcaccgt tgtcgatgtc ggcggcggtc | 780 |
| gtggtcatct cagccgacgg gttcgcaaa agcatcccca cctcaggttc atcgtacagg | 840 |
| acctgcctgc cgtcattcac ggagttgagg acactgataa agtcaccatg atggagcatg | 900 |
| acattcgtcg ccccaaccca gtgcgtggcg ccgacgtcta tcttctccga tctattctac | 960 |
| atgactatcc cgatgctgca tgcgtggaaa tcctctccaa catcgtcacc gccatggacc | 1020 |
| caagcaagtc gcgcatcctt ctggacgaaa tgattatgcc cgatcttttg gcgcaggatt | 1080 |
| cgcagcgctt catgaatcag atcgacatga ctgttgttct gacattgaac gggaaggaga | 1140 |
| ggtctaccaa ggagtggaat tcgcttatta cgacggtaga tggtagactg agactgaga | 1200 |
| agatatggtg gcgcaaaggc gaggaagggt ctcactgggg cgttcaacaa ctgcgtttgc | 1260 |
| gcaagtaggg gaatgcaatg gagatatcct tgggtctgtc agaagaacgg ctgagctatg | 1320 |
| attggcgaac acccttgccc taattcgtag ggtttgattt caagacaatt agacagtcct | 1380 |
| atacgtagaa ggagttcacc aaatcaatac tttcccactt ggca | 1424 |

<210> SEQ ID NO 4
<211> LENGTH: 9969
<212> TYPE: DNA
<213> ORGANISM: Aspergillus parasiticus
<220> FEATURE:
<221> NAME/KEY: unsure
<222> LOCATION: (1035)
<223> OTHER INFORMATION: nucleotide unknown
<221> NAME/KEY: unsure
<222> LOCATION: (1087)
<223> OTHER INFORMATION: nucleotide unknown
<221> NAME/KEY: unsure
<222> LOCATION: (1114)
<223> OTHER INFORMATION: nucleotide unknown
<221> NAME/KEY: unsure
<222> LOCATION: (1117)
<223> OTHER INFORMATION: nucleotide unknown
<221> NAME/KEY: unsure

```
<222> LOCATION: (1131)
<223> OTHER INFORMATION: nucleotide unknown
<221> NAME/KEY: unsure
<222> LOCATION: (1199)
<223> OTHER INFORMATION: nucleotide unknown
<221> NAME/KEY: unsure
<222> LOCATION: (1339)
<223> OTHER INFORMATION: nucleotide unknown
<221> NAME/KEY: unsure
<222> LOCATION: (1388)
<223> OTHER INFORMATION: nucleotide unknown
<221> NAME/KEY: unsure
<222> LOCATION: (1438)
<223> OTHER INFORMATION: nucleotide unknown
<221> NAME/KEY: unsure
<222> LOCATION: (1468)
<223> OTHER INFORMATION: nucleotide unknown
<221> NAME/KEY: unsure
<222> LOCATION: (1783)
<223> OTHER INFORMATION: nucleotide unknown
<221> NAME/KEY: unsure
<222> LOCATION: (1827)
<223> OTHER INFORMATION: nucleotide unknown
<221> NAME/KEY: unsure
<222> LOCATION: (2933)
<223> OTHER INFORMATION: nucleotide unknown
<221> NAME/KEY: unsure
<222> LOCATION: (2993)
<223> OTHER INFORMATION: nucleotide unknown
<221> NAME/KEY: unsure
<222> LOCATION: (2994)
<223> OTHER INFORMATION: nucleotide unkown
<221> NAME/KEY: unsure
<222> LOCATION: (3068)
<223> OTHER INFORMATION: nucleotide unknown
<221> NAME/KEY: unsure
<222> LOCATION: (3185)
<223> OTHER INFORMATION: nucleotide unknown
<221> NAME/KEY: unsure
<222> LOCATION: (9599)
<223> OTHER INFORMATION: nucleotide unknown
<221> NAME/KEY: unsure
<222> LOCATION: (9619)
<223> OTHER INFORMATION: nucleotide unknown

<400> SEQUENCE: 4
gaattcactg taggaaggac ggcgatagaa ggccaagaca tcctgccgtg ccatgttcca     60
ccacgagcca tagcgtcgcg acttctttac atccagcatt ggtgatatcc cggcgagaaa    120
ctcggggtc  atttcggccg tccagagatc gactttctgc tgaagttccg ccacccaaag    180
catccgactg agaggcttga daccccgaca atcaatttg  taagtattct tgcttagcgc    240
ttgggaactt gttggaactc ccgagcccta cgggtgcccc cttgggaaaa ctccggctac    300
ccacagccgg atcaatcgcc gacgattccc atagcatctt cattcatagt gtcttgtctc    360
gggcggaggg tgatgccaca cgattcgggg tacatagatg acacgttgtc ccagtactgt    420
tccgctgcgc tcgatgaagc taaacgccat ggggggttctg acgcaatggc gtagagcagc    480
accgctgttt gtcgcaaggg tcctagaccc cacttgtttg ctaggtgggc tcgaatagcg    540
ttggcgttga agtcactagg catcttggac gagattagtt tggcaactgc cgcggaggac    600
gttttcccca gttgcactgt tgggttggcg tcgccaaagt cccgcagcag gatctgctct    660
ggtgcatccg ggatggagct gaactccttg tctatatccc ccacgagctc gttctgcaga    720
gaagaccgac ctggaagatg acgtcagaca tagggtactg ctgcgcgtag gaaacatggc    780
cataccaccc gacaactctt tgattgactt tgatgtagga agctgagcaa ttgccgtctt    840
cagctttctg gcaacaagag cctgaacaat ttgcactcga gatagcgcca catccgtcga    900
tcacgatctt ttggaagcac ttattaggcg aaatatttgg ccgtttgggg gttagcgaag    960
```

```
gagggdtaga gagaggcggt tgctctttag gcccctcctc ggtgattggg gttacacctg    1020
gggcttgcct ctcgncatac tcataaacaa agattctccg cgtctaacga gcttgcgaga    1080
agctgantag aggaggcggc caatctcttc cctnggntga ccatgcctcg nacgcttttg    1140
ggggcatgtc cgccaggatg ttggacggac ccagctcgac gtagcgtgga agcagaatnc    1200
tggtatatat tgatcatcca tgccttctgt tctcatatcg atactccgtt ttagacacga    1260
cctgggcgat ccgccgctgg aataagatag gaatccttta ataacgcgtg aaatagtagc    1320
gctcatataa attagtatng gttcaatgcc cgaacaccta agttgatcca cgggccattg    1380
atactttnca gccccaaccc ccgaatcccg actttccgtc gttgacttga aaggaagncc    1440
cctcggcttg tcaagattgc cagccggnct gtgcacaaga cagactaggc cgaggcttgg    1500
agcccgaaaa tctctttctt tctcccttgt cctggtaaaa gtttacatac tccccttttaa   1560 ctgctacagc tttactctaa ggtgagtgtt tgcgtctaag gatgggttcc attagtaggg    1620
aacatgagtc aatccccatc caggccaccc agagaggcgc gcccggatct gcactgcttt    1680
tggaggtcaa gggtctaaca atctggacgt gttaaaaggt ctactcgagt taaacaagcg    1740
gtatggccca agatctggat gagctactaa gacgtgcatc ccnacacgct ttcgcagctg    1800
gcatcttccc ctgctccaat aagacgntcc acgaaccctg gggtttcgac ctccgacaat    1860
ggctgaccca caccggaggt tgctcctagc aaagaaattc ttgccctgcc accacgaagc    1920
tttcccttaa atacgttact tagcctggcg ctctattgtg caacttgtcg agagcttgaa    1980
cttgatcctg ggcatttcga tccctccttc atagttccac ggggcattcc caaggcatat    2040
tggcggcggt ggccatcacc caagccgaga gctggccaac cttttatgac gcctgcagga    2100
cggtgctcca gatctctttc tggattggac tcgaggcttc cctcttcact ccatcctccg    2160
ccgcctcgga tgccatgatc caagattgca tcgaacatgg cgagggcctt ctttcctcaa    2220
tgctaagtgt ctccgggctc tccccgctcc caagttgagc gagtaattga gcacgtcaat    2280
aaagggctcg gagaatgcaa ccgatgggtt cacttggccc tgggttaact cccacgaaaa    2340 gtccgtctt agcgggacca ccctcaaatc cttatgggcc gtttggcttc catgtcccga    2400
cgggatccaa gagcaggaca aaatgacctc cgaccaagtc gccgtttccc ttggttcccc    2460
gcaaccccgg aaagcctata gtggatatat tatttcttcc catatccgca ccatttcaca    2520
cagcgtactt cgacggtgtt caagatcgcg ttatcgaggg tttgagctct ggttcgttgg    2580
gtctccattc catcaaaatc cccctctatc acacgggcac tggggagcaa cctacaagaa    2640
ctacaaccac atcagctaat cccgactctt atccgcgcca ttaccgtgga ccaattggac    2700
tggccgctgg tttgccgggg cttgaacgca acgcacgtgt tggactttgg gacctggaca    2760
aaacatgcag tctttattca aggagctcac acaaggaaca ggtgtatcag tgatccagtt    2820
gactactcaa tcgggaccaa aacccgttgg aggccatctg gcggcagtga actgggaggc    2880
cgagtttggc ttacgacttc atgccaatgt ccacggtgca gctaaattgc gcncccgtat    2940
cacaacccct tggtgggaacc gtcctgtgaa ggtagccggg atgacacctc gcnnggtgcg    3000
gtgggacttt ttcccttccc ttgctcaaga tggaaaccag gtcggactgg gtggtggtgg    3060
gtaccacnca gagccccagt tcgaggccga gattcggcgg ctgccaactt gcatccaaga    3120
agattatggg atcacctgca atcccccccc acgccaagcc tacgactttt tcctggcaga    3180
ttctntttca tccaaggatc tggttcccca gggagttacc cgtggaagga atcaccatcg    3240
gcgccggcat cccttctccg gaggtcgtcc aagaatgtgt acagtccatc ggactcaagc    3300
acatctcatt caagcctggg tctttcgaag ccattcacca agtcatacag atcgcgcgta    3360
```

-continued

```
cccatcctaa cttttttgatc gggttgcaat ggaccgcagg acgaggggga ggacatcatt    3420
cctgggggag acttccatgg acctattctg gcaacctacg ctcaaatccg atcatgtccg    3480
aatattctcc tcgttgtagg tagtggattc ggtggaggcc cggacacgtt tccctacctc    3540
acgggccaat gggcccaggc ctttggctat ccatgcatgc ccttcgacgg agtgttgctc    3600
ggcagtcgca tgatggtggc tcgggaagcc catacgtcag cccaggcaaa acgcctgatt    3660
atagatgcgc aaggcgtggg agatgcagat tggcacaagt cttcgatga gcctaccggc    3720 ggcgtagtga cggtcaactc ggaattcggt caacctatcc acgttctagc tactcgcgga    3780
gtgatgctgt ggaaagaaca cgacaaccgg gtcttttcaa tcaaagacac ttctaagcgc    3840
ttagaatatc tgcgcaaccg gcaagaaatt gtgagccgtc ttaacgcaga ctttgcccgg    3900
ccctggtttg ccgttgacga cacggacaga atgtggagct ggaggacatg acctacctcg    3960
aggttctccg ccgtctgtgc gatctcacgt atgtttccca ccagaagcga tgggtagatc    4020
catcatatcg aatattactg ttggacttcg ttcatctgct tcgagaacga ttccaatgcg    4080
ctattgacaa cccggcgaat atcactgaca tcatgtcggg tggaagagag cctgaaggat    4140
aaagcatacc gcacgcttta tccagaagat gttctcttct aatgcatttg ttcagccgac    4200
gtgacatcaa tgcccgtacc attcattccc caggttggat gagcgttttg agacctggtt    4260
taaaaaagac tcattgtggc aatccgaaga tgtggaggcg gtaattggac aggacgtcca    4320
gcgaatcttc atcattcaag ggccctatgc gttcagtact caatatccga cgatgagtct    4380
gttaaagaca ttttacacaa tatttgtaat cattacgtgg aggctctaca ggctgattca    4440
agagaaactt ctatcggcga tgtacactcg atcacgcaaa aacctctcag cagcgttccc    4500
tgggctcaaa gtgacgacaa atagggtcca agggctcata agttcgagaa agtaggagca    4560
gtcccgaaat ggacgttctt tttgagcata tgttctgact gtgaagtatg ggtggacatg    4620
tttgatgagt aaatcggtct ttagggaggt tctgttgata atgtaggaca gtcccgaatg    4680
acgtcttttt gagcatattg tcggaactgt cgaagtcatg gctcgaacat gttgatgagt    4740
aaatcggtct ttagggacgg ttctcgtctg cataacccca attcggcgtg acactccagc    4800
tccagcgcgg cgacaccatc gaggtgcttt taacagcaga ctcggaaatt cgcaagattc    4860
gacttatttc acaacggggg atggtggatc cacttctaag gtcgtattag agatagtctc    4920
taacgacgga caaagagttt tccgcacctt ggcccctaac atcccactca gccccgagcc    4980
cagcgtcgtc ttttgcttca aggtcgacca gaagccgaat gagtggaccc ttgaggagga    5040
tgcgtctggc cgggcagaga ggtacaaggc attatacatg agtctgtgga acttgggctt    5100
tggtaacaag gcctctgttt tgggtcttaa ttcgcaattc tcgggacaag aactgatgat    5160
cacaacggac aagattcgtg atgcgaaagg gtactgcggc aaaccagtcc tcttcagctg    5220
cagtcatgga accccaagg atgtgtacct atcgactact gcgtggtcat cgcctggtct    5280
gctcttacca agcctctgat ggtctcctct ctgaaatgcg acctcctgga tctgctccac    5340
aggctataag cttcactatg tccatctgtc aaaccattgc gggtgggcta tattgtcaaa    5400
acctcatccc gtatcctagc ggtctcggtg agactagggg aactatgctg acggtgtcgg    5460
cggacattca gcgccaggga caacatgtaa gtcactgtca aatcagattt ctttctcgga    5520
ggcccccgtt ctggcatgtg aaaccccttt cgaacgactg gagcctgaaa tggttgtcca    5580
tgtcgactct gaagtgcgcc gtgctatttt acacagccgc aagtggctca tgcgagaaga    5640
tcgcgcgcta gatctgctag ggaggcagct cctcttcaga ttaaagagcg aaaaattgtt    5700
```

-continued

```
caggccagac gccagctagc actgttacag gtaacaggtt ccgtgttcag ctacagcccc   5760
gatggtcaac gacatgcttc ggtcgcgtat acttcgaaag cgagtcttgt acagggaacg   5820
tggtgatgga cttctgcacc gctaccagcc cgggcgcacg tgctggagct cgaacatccg   5880
ggtggacggc acctcttgac ctgtggcagt aagaggtcct cgacgcagcc aatcctgaca   5940
gcgtctccct cgatcataat cccatccatg tttgtccggc cttttgccata cgctggtctc   6000 tcgggtccca ttgtccatgg gatgaaacct ctgccatgat gcgcagtaat tgccgaatgg   6060
gccatcggag atgcagaccg gtctcaggtt ccggagctgg cataatcacc ttgcaagtca   6120
cccgtccacc ccatagcgac ccttcttgcg ggtggaggcc ttgcagcaat taaggccatt   6180
gggaaggtac caggaggaat gttgggtttt tggaaaaggt tacaaagcca ttttggaaac   6240
gaaaggacgg aaagaacgta gcggagcaga tgcccatgtt gagcaggaaa ctacggctta   6300
cgtcttctgt ggccagggca gtcaacggac aggggatggg aatggacttg tacgtcaact   6360
gtccggagcg taaacgttgt cgcgcgccga caagcatttg tgggagaaat atggtatggc   6420
atttgctatc tcgccgtctg tagctcgtac ttaaattttt caccagggtt ctccatactg   6480
cattgtgcaa acaaccctc cagccctcag gtgttcactt tggcagccag gagggcgccg    6540
tattcgtgcc aacctatctg cgcgagtgat gggacagcct accgatagat ggtagacatc   6600
cgcccatact gaagggattg acgcggaatt cgacctcgta caccttctcc tatcccaggg   6660
gctgttgatg tccacccgtt cgcccagccc gcactggcgc tgatggaaat ggctcagttc   6720
gaatggctca aagccaggga gtcgttcaga agggtgcgcg gttcggacat tcgttgggag   6780
aatatccgcc cttggagctt gtgcttcctt cctctcattt gaagatctca tatctctcat   6840
cttttatcgg ggcttgaaga tgcagaatcg atgccgcgat gccaaccgca caccgagtat   6900
ggaatgttgg ctgccgatcc atcgcggata ggaaaaggtg atatctagct tctctctgtg   6960
ctgctcggtc tgacatgggt gcatgtttcg aggaagcgag tctgaaatgt cttgtccata   7020
tcattcaaca ggagaccggc tggttcgtgg aagtcgtcaa ctacaacatc aactcgcagc   7080
aatacgtatg tgcaggccat gtgggtgatc tcctatcctg tcttccctca tccttgactt   7140
tccttgttac tgatagtgtt cccctcgacc cgactgcagt tccgagccct ttggatgctg   7200
ggtaagatat gcgatgacct ttcatgccac cctcaaccgg agactgttga aggccaagag   7260
tacgggccat ggtctggaag catgtccgac ggtggagcag gtgccccgcg aggatcgcat   7320
ggaacgaggt cgagcgacca ttccgctgcc ggggatcgat atcccccat accattcgac    7380 catgttacga ggggagattg agccttatcg gtgaatatct gtctgaacgt atcaaggtgg   7440
gggatgtgaa gccgtgcgaa ttggtgggac gctggatccc taatgttgtt ggccagcctt   7500
tcgtccgtcg ataagtctta cgttcagact ggtgcacggc atcacaggta gtcctcggct   7560
tcattccctg cttcaacaaa tggcgtgatc atatccccgt atgaggttac attggtcttg   7620
gtcttgattc tacttgacgg gctgcttttg cttttctacat gaataccacc tgtttaaaac   7680
atgttcaacc caaagacttc cctattgaaa cactgcggtt cattgagtga ccgtgttgct   7740
tagttgaaca ttctttgata tattaaccat ccagaatgct cccgaggatt gcttagactc   7800
tttccgccta gtagtagtcg gccacgatga accgatccta ttggcgaccg ctgcgtagaa   7860
gtcgatgtag gaaagtgcac gtgcatcgca gcggaatgga aatcatgacg caagataagc   7920
agaccaacgc ggaagatgat cgacaactgt atgtattact ctatcttggg aaggtggatc   7980
ctcgggcatc caaggtgtca atccagcttc ttgaatagta attcctttgc catcgtactt   8040
tctgggcttc ttgaatagta attccttcat cgtacttctg gttttcgctt tccgacacat   8100
```

```
gctctgcccc ccctcctact gggtcctgtc accggagtcc gagaccaatt tcgtgcatct    8160
gatcatacga atggcttata ggagaataga gtggatcatg ctgaccctag taatgtcaaa    8220
catatatgat tctaatatta tatggcttct atttttttt aggattttg aattttaaa      8280 tctgatccgg ataacagacc cggaactaaa aaatatatat ttctgttttc aacatataat    8340
ttactattac tctatcttta gctataagga aaatttaact aattcacga tatagattgt     8400 atagactgtt caagattcgt attattagta ttctatatag aaatttcact ccaagcaatt    8460
tgagggttta cagggaatca ttgaattctt gatcattaca acgggtcggt tattttcgat    8520
catttcgttg gacggatcac gggtacccca cctgagccga gcgctctcag ggatttaggg    8580
gcttgcattc gtagggccct aacaagtaac aacacgttcc accaacacca acgactcttc    8640
accctgcttc ttgtggggag caatgattga tcgctcaatc caagaattga aacctacacg    8700
ggcgatgaat ttgtaaaagt tgcatgatcc gtgcatcgta atcgccactg gagcgcgtgt    8760
gttgatcgat cggccagtct cgccctttca aggccggttg atcgaagaga atcgtggat    8820 gcaatgtaac catgacaaag acggatcctg cgagatggc ggttgccacg atttgctccc    8880
cccctgcacc caaaaaggcg caaaaacact aatcgcaagg gggtgagggg cagcgggtga    8940
gctgatatca tgtcgatatc attccaatct caatggagag ggaaacaggc ctgtcatctg    9000
ctcctggcgg tggggctttt cttcattctc gatgcaggta atcgataatg tcggaggaca    9060
cggcgcgcaa gcggtggcgg agatttgctt cgaggccact aaaaccgagt agtgagaaag    9120
gggacgctgg atggtgcgcc ggtatccctg ctgcatcgtc tccaccctcc ttgcaggcgc    9180
ttggccaata ggttcaccag cgactgcact cggtgcagtt cgctcagaac aagctgtgcc    9240
gccactcgcg gctggtcttc ctcatccaca caatcctcgc ccaccatact agggtggtgc    9300
agcacgcgct cttccgtcag acagccactg gacacggtgg cgggactgtt gctacagctg    9360
ccactgttgg tttctccacc cgccgccgtt gaggtacact gggtgcctgc tgccgcagca    9420 taccaccca gcaccttgag aacgataagg ccgaccatgc tcagcaagta gccatcctgc    9480
gcgcacgaac acccgaggat attccggacc gcatcggtag ccttcttgtt ccccgagatg    9540
accatatcag tcggtcatca ggttgcacga actgtcctca ccgtcccgtc agccgcagnt    9600
gacagcccag cggggcgtng gggaagagga agtcagtgtt tggtggtgct agcgaaccgc    9660
atcggtagcc ttcttgttcc cccgagatga ccatatcagt cgtcatcagg ttgcacgaac    9720
tgtcctcacc gtccgtcagc cgcagctgac agcccagcgg ggcgtggggg aagagccagg    9780
tcagtgtttg tagtgctagc gaaaagcagc aatagcgcgc ctgaaacggt ggcagtgggc    9840
ccgactcgag gaacgggtcg atcatggggg tccccacttc caaaaacgcg tcgaaaagac    9900
tccccgtcga ctcagccaag aaatcggcat ggtttccgtg ttccattgac tgcaaaagcc    9960
cccgaattc                                                            9969
```

<210> SEQ ID NO 5
<211> LENGTH: 2844
<212> TYPE: DNA
<213> ORGANISM: Aspergillus parasiticus

<400> SEQUENCE: 5

```
ggatccaggg ctccctggag ctcacgcagg tgctaaagat ctagcttcga ggaaacaagt     60
cttttctggg ttctcagccc gcccatgacg gactacgtta tcttgagccc gaggcatgca    120
tgcaggcggg ccagctagct gaacattatt tgttggtctt ggtttgcttc gttaaaccga    180
```

-continued

```
tcacgcagtt ctctggtcac ccggtttcag cctcggtacg taaacaagga acgcacagct    240
agacaatcct tgggccaagt cagaacccct cagctggtga caggagtgta catacattta    300
ggcctaagtg cgaggcaacg aaaagggccg gctactctcc cggagcaagc cttcaccttg    360
tgtgttttct ttcccgcttt caattgagaa ttcctgaatt ccttcctcac ctccacgatg    420
gttgaccata tctcccccg gcatctccc ggaccgatcc gttcctccca gactcgccgc      480
gcccgaaagc tccgggatag ctgtacgagt tgtgccagtt caaaagtgcg atgcaccaag    540
gagaaaccgg cctgtgctcg gtgtatcgaa cgtggtcttg cctgtcaata catggtctcc    600
aagcggatgg gccgcaatcc cgcgcgctccc agtcccttg attcaactcg gcgaccatca    660
gagagtcttc cttcagccgg gtcggaacag ggacttccgg cgcacaacac gtactcaacg    720
cctcatgctc atacccaggc ccacactcat gctcattctc atccgcaacc gcatccacaa    780
tctcatcctc aatcgaatca accaccacac gctctgccca ccccaatgg tagcagtagc    840 gtctccgcca tcttttctca ccagagtccc ccgccactcg tggagaccca gggccttgga    900
ggagatctgg ctggtcaggc gcaaagcacc ctgtcttccc taacagtcga ttcggaattc    960
gggggctctt tgcagtcaat ggaacacgga accatgccg atttcttggc tgagtcgacg    1020
gggagtcttt tcgacgcgtt tttggaagtg ggaccccca tgatcgaccc gttcctcgag    1080
tcggccccac tgccaccgtt tcaggcgcgc tattgctgct tttcgctagc actacaaaca    1140
ctgacctgcc tcttccccca cgccccgctg gctgtcagc tgcggctgac ggacggtgag    1200
gacagttcgt gcaacctgat gacgactgat atggtcatct cggggaacaa gaaggctacc    1260
gatgcggtcc ggaagatcct cgggtgttcg tgcgcgcagg atggctactt gctgagcatg    1320
gtcgtcctta tcgttctcaa ggtgctgggg tggtatgctg cggcagcagg cacccagtgt    1380
acctcaacgg cggcgggtgg agaaaccaac agtggcagct gtagcaacag tcccgccacc    1440
gtgtccagtg gctgtctgac ggaagagcgc gtgctgcacc accctagtat ggtgggcgag    1500
gattgtgtgg atgaggaaga ccagccgcga gtgcgcgaca gcttgttctg agcgaactgc    1560
accgagtgca gtcgctggcg aacctattgg ccaagcgcct gcaagaaggt ggagacgatg    1620
cagcagggat accggcgcac catccagcgt ccccttctc actactcggt tttagtggcc     1680
tcgaagcaaa tctccgccac cgcttgcgcg ccgtgtcctc cgacattatc gattacctgc    1740
atcgagaatg aagaaaagcc ccaccgccag agcagatgac aggcctgttt ccctctccat    1800
tgagattgga atgatatcga catgatatca gctcacccgc tgcccctcac cccttgcga    1860 ttagtgtttt tgcgccttt tgggtgcagg ggggagcaa atcgtggcaa ccgccatctc      1920
gccaggatcc gtctttgtca tggttacatt gcatccacga tttctcttcg atcaaccggc    1980
cttgaaaggg cgagactggc cgatcgatca acacacgcgc tccagtggcg attacgatgc    2040
acggatcatg caacttttac aaattcatcg cccgtgtagg tttcaattct ggattgagcg    2100
atcatcattg ctccccacaa gaagcagggt gaagagtcgt tggtgttggt ggaacgtgtt    2160
gttgcttgtt agggccctac gaatgcagaa caagccctaa gccctgagag cgctcggatc    2220
aggtggggtc ccgtgatccg tccaacgaaa tgatcgaaaa taaccgaccc gttgtaatga    2280
tcaagaattc aatgattccc tgtaaaccct caaattgctt ggagtgaaat ttctatatag    2340
aatactaata atacgaatct tgaacagtct atacaatcta tatcgtgtaa ttagtttaaat   2400 tttccttata gctaaagata gagtaatagt aaattatacg ttgaaaacag aaatatatat    2460
tttttagttc cgggtctgtt atccggatca gatttttaaaa ttcaaaaatc ctaaaaaaaa   2520
atagtaagca tataatatta gaatcatata tgtttgacat tactagggtc agcatgatcc    2580
```

-continued

```
actctattct cctataagcc attcggtatg atcagatgct cgaaattggt ctcggactcc      2640
ggtgacagga cccgatagga ggggggggcag agcatgtgtc ggaaagcgaa aaccagaagt     2700
acgatgcaag gaattactat tcaagaagct ggattgacac ttcgggattg cccgaggatc     2760
caccttccca agataggtaa tacatacagt tgtcgatcat cttaagcgtt ggtatgctta     2820
tcttgcgtca tgatttccaa gctt                                            2844

<210> SEQ ID NO 6
<211> LENGTH: 4310
<212> TYPE: DNA
<213> ORGANISM: Emericella nidulans

<400> SEQUENCE: 6
atgccccaga agggagcacc gctgtaggcg caagctgacc gagttgggag cgcaaagcgt       60
ggccgcggct gcgattgcgc tcgcatacct gcttcacaag tcgccgtacg ttttcccggt      120
gatcgggtgc cggacggtcg agcagctgga ggcgaatata cgcctcggtg tagagctcag      180
tgatgaggaa atgtacgaga ttgaagacac gatcccttt gatgtcggct tccccatggc       240
gttcttattc gaatcgcccc agcagaagta ccgtagtgat atgacgacca ggcatatctg      300
gcaggttacc tgcaatgccc ggatcgagag tgtgcctaag ccgagagtat gtatctctca      360
acctgaattt atgatttcgc taatcgaact taccagccta tcgagccaaa gcagggtaca      420
agcagatgga tcggaagtag ttctcggtag cattagccaa gcatcgggtc ccgagcgttc      480
aagtatttta tatatgagcc ttgtttcctt cctatgtcat ggtagccagt atccataagg      540
tataggaatc aaccatgtcc tcctccgata attaccgtct cgatggaaaa gtcgctctgg      600
taactggggc tggccgcggc atcggagcag ccatcgccgt agccctcggt cagccgggcg      660
cgaaggtcgt cgtcaactac gctaactccc gtgaggccgc agaaaaggtc gtcgacgaaa      720
tcaagtcgaa cgctcagagc gccatttcca ttcaagccga tgtcggtgac cctgatgccg      780
tcaccaaact gatggatcag gccgttgagc acttcggata cctggatata gtctcatcta      840
acgcgggaat tgtctcgttc gggcatgtca aggacgttac gccagatgta tgcgtcccat      900
ctccttacga aagtcctgta gagctctgac ctcagcagga attcgaccga gtatttcggg      960
tcaacacgcg cggacagttt ttcgtcgccc gcgaggcgta tcgccatctg cgtgaaggcg     1020
gacgcatcat cctcacaagt ccaacacag ccagcgtcaa aggcgtcccc aggcacgctg      1080
tgtactcggg ctctaagggg gcgattgaca cctttgtgcg gtgcctagct atcgactgcg     1140
gcgacaagaa gatcacggtc aacgcggtcg ctcccggcgc catcaagacc gatatgtttc     1200
tatccgtgtc gcgagagtat atccccaatg gggagacttt tactgatgag caggtggatg     1260
aggtacgttt gtctttgtgt ctagtatcta cggcggctgc taactggaca gtgtgccgcg     1320
tggctgtcgc cgctaaatcg ggtcggatta ccggttgacg tggcccgggt ggtcagcttt     1380
ctagcttcag atgcggccga atggatcagt ggaaagatta ttggcgttga tgggggggcc     1440
tttagataag tcacatcata tacttgaact atataggta gacatgcaat gttcgctccc      1500
cgctcgctta ccgatatctg ccgatcatcg tcagcaacca ttaggtcacg aaaaaaagag     1560
tatactaaga gtaaacatcc gtgcatggta tgaacttagt tgggtacacc gcagttagtc     1620
acaccgtact taagtacact cagcgattca cttaggcggc tgaatcggca tttcatactc     1680
tgccagcacc ggaggcccag caacatcaac aacaataggc aaagcatgca cacgctcaaa     1740
ccaggtagat aggttgcggt gctcatccct ccagcgttta tcaaggaaaa accggaatgc     1800
```

```
gccctgcaca atcccgagca caaacagatc agctaggctg agggtttccc cgaccaagta    1860
ctctcgccca caaagatggt tgtcaagaat ctttagccgt gctaaagtgt catctttgct    1920
ttgatatatg ttgtcagcat tgaagttggc tcgtccgatg agcgggttga accagccccc    1980
taacgctggg aggatttcgg tgatcccgaa ggccatccag cgaatgatgg aggcatattc    2040
ttgtccggta gtcccaagta aagtcgtatt tgaatcttga gatgttacta tacctcttag    2100
tcaggaattg aatagatgga attgcagtag cagcatggta ccatagagag caatagcaat    2160
agattccgtc aatacgtacg cgtcggcccc cacaaacgta ggaatcttgc ctagagggtt    2220
gagctggaga tactcttcgg tagcatcttt gaatgaagtg atggtcttga ttttcagagg    2280
caaattgttc gcttttgcaa tcgcaagaat cgccagcgac cgcgggttga acggcgagt    2340 gtacagagtg ccgaacggca ttgcagaaat attctcaatt cagagctgat tctcgtattg    2400
tatgcttgtg caacctgct aaatacaaat actgacagca aatcaactat atgtcaagac     2460
catgcccttc agctgtccgc gtaaccctaa cttcccccag acaacggcc ttcatctttc     2520 cccgatccgt gaaacggtcc tcgtccgcca taacttcggg gctgctcatg acggggacaa    2580
actcctcgaa ggtggcttgg ctcgcaaatt ggacaacagc aaatgcgtcg aaggtcaaat    2640
cgatcgagtc gccggccagc ggggtgaccg gttgctgcag gtagtgtcgg gtgtggctga    2700
ctggaaaggc cctcccgccg agtcgttgca gcaggggat atgttcggtc tcccagtggt     2760
tacgaaattc gctgggtgtg aggtcgccgc gacgggctac aagaatcaag acagtgaaca    2820
tggtggagtg aaagtgctgt gtatgtttgt ccacacttgc ttccagaatc tcgcgcaata    2880
cgcctctata tatggcctgt ccctatctcg gtcgccgaac gaactaaaca attattcaga    2940
gagactcttc ttacattttt gtcattgttg ccaaagtcac ttcactcatt gctgtcctcc    3000
aaccatgtac acaactatca tcacagcggt atgcgtgcta ttcgctcttc acctcctgga    3060
cagcttctat caagcgcggc aggaggtatg ggccctccag cgggcaaacc tagtacgagc    3120
cctctgaccc aatgattggc tagaggacga ttaactggtg atacaagccc atgccttctt    3180
tcagcctgct gaccggccac tttggtgccc tcaaacaaac catcgatggc atgccgccca    3240
acgcaaccct gcatagcatt atgctgaaat tgtcgcaaaa gttccgctca gggatgttct    3300
acatcaacat gtggccattc agcggtacat ggctcgtggt cgcaacaccg tctggcgcgg    3360
cccagatcca gagtctgaat cttcgaagc cgccgctggt gcgaagaccg ctggagacta     3420
tcaccggggg cccaagcttg atgagtatgc atggtgaaac atggaaacgg tggagggcac    3480
tgtttaatcc aggctttaac cccaactact tgattgggct ggcgccgctg atcgccgatg    3540
aggtcgttgt tttttgcgag cagctacgga agaaggccag aacaggaaca gttttccagc    3600
ttgaaccgct cactctgagg ttgacagttg atacgatttg ctctgtgacg ttgtatgtgg    3660
ttactcccgt tgggcgatgg ccctttctaa cccctgactt agagattcac agctccacca    3720
ccaaactcag gaccaccccc ttgcctcagc gctgcaacgg cagatcgaat gggcctcgtt    3780
tggaactacc ttcaacccct ttaaggcggt acctgaccgt gcggcctctg tgatgtggt     3840 acaataaccg ccttatgaac cgcttcatcg accaagaggt tgaccgagcg taccgggagc    3900
agtctggccg tcagtcgaaa tccgtgatct ccctcgccct cagagattac atgaaagaga    3960
aagatggaag tctggaagac ttcaaacgac gtgttcgcc acagttacgg gtctttctct     4020
tcgcaggtag agatacaacg agcagtacac tgctctatgc attctacctg ctttcccgac    4080
atccagaggc cctagctaag gtgcgcttag agcacgacca ggtcttcggc ccatatcatc    4140
aacaagtaca cgagaaaatc caccaagatg cgaaactcct caaccaactc ccctacacaa    4200
```

```
cagctgtcct taaagagact ctgaggctct tccctccgtc tgcctccatg cgtgaagcgg      4260
acccggcgtt gaaatcaccg acgacaacgg ccaagtatat cccactgcag                 4310

<210> SEQ ID NO 7
<211> LENGTH: 1799
<212> TYPE: DNA
<213> ORGANISM: Gibberella pulicaris

<400> SEQUENCE: 7
tgtacctatc gcttgcgtag ctctttacta catgtgccga gctaaagata aaatcggact        60
aaagattcgt cccgggagcc gagctaaaga taaaatcgga ctaaagattc gtcccgggag       120
ccgaatgcta tctcaagctc gtcgtgttgc aggggatgga agacctccag tgtacgtcac       180
ggtctctatc actacgaatt tactgggaag gctatttgca ttaacgtcaa gttaatcatt       240
aggcctaaca acacaagcac aactaaagat tgtggatggt tgacatttac catatgctga       300
tatatagttg atagcaacag cactttgcaa tagaacaata atagcgattt gacttgaaaa       360
ctcaccaaga atcgttacca attattatac cattatcatc atggagaact ttcccactga       420 gtatttctc aacacttctg tgcgccttct cgagtacatt cgataccgag atagcaatta       480
tacccgggaa gagcgcatcg agaatttgca ctatgcttac aacaaggctg ctcatcactt       540
tgctcagcca cgacaacagc agctgctcaa ggtagaccct aagcgactac aggcttccct       600
ccaaaccatt gttggcatgg tggtatacag ttgggcaaag gtctccaaag agtgtatggc       660
ggatctatca attcattaca cgtacacact tgttttggat gacagcagcg atgatccgta       720
tccggccatg atgaactatt tcaacgatct tcaggctgga cgagaacagg cacacccctg       780
gtgggcgctt gtcaatgagc actttcccaa tgtccttcga cattttggtc ccttctgctc       840
attgaacctt atccgcagca ctcttgactg taagtaccct ggctctatta tttcaccacc       900
ccaataagct aacagtgatg gaattgcagt ttttgaggga tgctggatcg agcagtacaa       960
ctttggagga tttccaggat ctcatgatta tcctcagttt cttcgacgca tgaatggctt     1020
gggccactgc gtcggggcgt cttgtgtggcc caaggagcag tttgacgagc gaggtctatt     1080
ccttgaaatc acatcagcca ttgctcagat ggagaactgg atggtctggg taaatgatct     1140
tatgtcattc tacaaggagt tcgatgatga gcgtgaccac atcagtctcg tcaagaacta     1200
cgtcgtctct gatgagatca ctctccatga agctttagag aagctcaccc aggacactct     1260
acactcgtcc aagcagatgg tagctgtctt ctctgagaag gaccccccagg tgatggacac     1320 gattgagtgc ttcatgcacg gctatgtcac gtggcacttg tgcgatcaca ggtaccgcct     1380
taatgagatc tacgaaaagg tcaaaggaca aaagaccgag gacgctgaga gttttgcaa     1440 gttctatgag caggctgcta atgtcggagc cgtttcgcct tcggagtggg cttatccacc     1500
tattgcgcaa ttggcaaaca ttcggaccaa ggatgtgaag gatttgaagg atgtgaagga     1560
tctgaaggag attcagaagc tccttctgag ctcaattgag ctagtggaat gaccgacggt     1620
gagatggaag tatgttttgc gggtactcgc taggagaata ctggtcgttt atcatgatta     1680
caaatagctt ggttgtgttt ttattagcat ttacagttga acaaggataa ttcctactga     1740
ataggcagct gaaactgatg tctgtaactc agcctgttc gttatccgct tgcctgcag      1799

<210> SEQ ID NO 8
<211> LENGTH: 2182
<212> TYPE: DNA
<213> ORGANISM: Aspergillus flavus
```

<400> SEQUENCE: 8

```
ccccttgacg cccgcacaac gaacaacttg acgttcctca ccgctcaact tcaaggccat        60
cttcctcct tctctcttct cctcttcctt ttacctactc cccgtcgact gtctccccca       120
gtctatccaa caaccttct ccaacgacct cttcgccgtt ttcaaaccca ccttttccta       180
ccaacaacgc caaatcccc tccacaatgc gtgagatcgt atgttgctcc ctaccccgg        240
tgggggaga agtctgctca aaagcccta tccccccccc ctgataggga ccccacccgt        300
tctccaatac tacaaggttg ctgacggagt ttgtttcatc atataggttc accttcagac      360
cggccagtgt gtaagttcga ctatgatttg atgtctagca ggaccatggc gacggatact      420
aaacgtatgt tggtgatagg gtaaccaaat aggtgccgct ttctggtatg tctcaatgcc      480
ttcgagttag tatgctttgg accaaggaac tcctcaaaag catgatctcg gatgtgtcct      540
gttatatctg ccacatgttt gctaacaact ttgcaggcaa accatctctg gcgagcacgg      600
ccttgacggc tccggtgtgt aagtacagcc tgtatacacc tcgaacgaac gacgaccata      660
tggcattaga agttggaatg gatctgacgg caaggatagt tacaatggct cctccgatct      720
ccagctggag cgtatgaacg tctacttcaa cgaggtgcgt acctcaaaat ttcagcatct      780
atgaaaacgc tttgcaactc ctgaccgctt ctccaggcca gcggaaacaa gtatgtccct      840
cgtgccgtcc tcgttgatct tgagcctggt accatggacg ccgtccgtgc cggtcccttc      900
ggtcagctct tccgtcccga caacttcgtt ttcggccagt ccggtgctgg taacaactgg      960
gccaagggtc actacaccga gggtgccgaa cttgttgacc aggttgtcga tgttgtccgt     1020
cgcgaggctg agggctgcga ctgcctccag ggtttccaga ttacccactc cctcggtggt     1080
ggtaccggtg ccggtatggg tactctcctg atctccaaga tccgtgagga gttccccgac     1140
cgtatgatgg ccacctactc cgttgtcccc tcccccaagg tctccgacac cgttgttgag     1200
ccctacaacg ccactctttc cgtccaccag cttgttgagc actccgacga gaccttctgt     1260
atcgacaacg aggctctgta tgacatttgc atgcgcaccc tcaagctctc caaccctct      1320
tacggtgacc tgaaccacct ggtctctgct gtcatgtctg gcgtgaccac ctgtctccgt     1380
ttccccggtc agctcaactc tgatcttcgc aagttggccg tcaacatggt tccttttccct    1440
cgtcttcact tcttcatggt tggcttcgct cctctgacca gccgcggtgc ccactctttc     1500
cgtgccgtct ccgttcctga gttgacccag cagatgttcg accccaagaa catgatggct     1560
gcttctgact ccgtaacgg tcgttacctc acctgctctg ctatcttgtg atgtggcccc     1620
tatttctat ttgttctatc ctctgttgtt tgaaaactga cctttcgata gccgcggaaa     1680
ggtctccatg aaggaggttg aggaccagat gcgcaacatc cagagcaaga accagaccta     1740
cttcgtcgag tggatcccca caacatcca gaccgccctg tgctccattc ctcccgtgg     1800
tctcaagatg tcctccacct tcattggaaa ctccacctcc atccaggagc tcttcaagcg     1860
tgtcggcgac cagttcactg ctatgttccg tcgcaaggct ttcttgcatt ggtacactgg     1920
tgagggtatg gacgagatgg agttcactga ggctgagagc aacatgaacg accttgtctc     1980
cgagtaccag cagtaccagg atgcctccat ctccgagggc gaggaggaat agtaaggatt     2040
cccattggcc ctgctctcgt gtatttgtgc taaccagttt gcagcctcga ggaggaggag     2100
cccccttgagc acgaggagta aatagcttcc agtcactaaa gactcggatt gatatctggc     2160
agcaataccc ttgataagtc ca                                              2182
```

ALKALOID THAT INHIBITS BIOSYNTHESIS OF MICROTOXINS AND METHOD FOR SCREENING FOR MYCOTOXIN INHIBITORS

CROSS-REFERENCE TO RELATED APPLICATION

This application claims the benefit of U.S. Provisional application Ser. No. 60/156,381, which was filed Sep. 28, 1999.

STATEMENT REGARDING FEDERALLY SPONSORED RESEARCH OR DEVELOPMENT

None.

BACKGROUND OF THE INVENTION (1) Field of the Invention

The present invention relates to an alkaloid compound that inhibits biosynthesis of particular products of secondary metabolism. In particular, the present invention relates to an alkenylene piperidine amide wherein the alkenylene alkenylene with one or more double bonds, which can be isolated from *Piper nigrum*, that inhibits transcription of fungus genes nor-1, tri5, ver-1, verA, fas-1a, omt-1, alfR and ipnA. The present invention further relates to a method for identifying compounds that inhibit the biosynthesis of mycotoxins in fungi. In particular, a method for identifying compounds that inhibit biosynthesis of aflatoxin in *Aspergillus* spp. and deoxynivalenol in *Gibberella* spp.

(2) Description of Related Art

Mycotoxins are a group of structurally heterogeneous secondary metabolites produced by a diverse group of fungal plants pathogens. Infestation of crops and food commodities by mycotoxin producing fungi is a serious problem in view of the immunosuppressive, carcinogenic, cytotoxic, and teratogenic effects of the compounds in humans and animals. One of the most economically important mycotoxins worldwide is aflatoxin, a polyketide produced by several *Aspergillus* spp. Aflatoxin is the best studied of the mycotoxins and much of the molecular biology of the biosynthetic pathway has been determined in *Aspergillus flavus*, *Aspergillus parasiticus*, and *Aspergillus nidulans*. *Aspergillus flavus* produces aflatoxin B1 and aflatoxin B2 whereas *Aspergillus parasiticus* produces in addition aflatoxin G1 and G2. *Aspergillus nidulans*, which is not considered to be an agricultural threat, has been used as a model genetic system for studies of aflatoxin biosynthesis because it produces sterigmatocystin, an aflatoxin precursor. The genes for aflatoxin biosynthesis are clustered in all three species. The molecular biology of aflatoxin biosynthesis is reviewed by Trail et al., in *Microbiol.* 141: 755–765 (1995). *Aspergillus flavus* and *Aspergillus parasiticus* are weak pathogens of corn, cotton, peanut, and nut crops: their effect is limited to a slight reduction in crop yield. However, the significant consequence of crops infected with either of these fungi is contamination by aflatoxin, which is produced under certain conditions during the infection. Traditional control strategies such as breeding crops for resistance to the fungi or chemical treatments of crops to prevent infection by the fungi have not been effective.

Aflatoxin is a secondary metabolite that appears to be the most potent naturally occurring carcinogen known (Council for Agricultural Science and technology (CAST), 1989). It is suspected of being responsible for the high incidence of human liver cancer in many areas of the world (Eaton and Gallagher, *Ann. Rev. Pharmacol. Toxicol.* 34: 135–139 (1994)). Aflatoxin is introduced into the food chain by preharvest and postharvest contamination of foods and feeds. Also, products from animals that have been fed aflatoxin contaminated feed may also become contaminated. Currently, the U.S. Food and Drug Administration limits the allowable amount of aflatoxin in food to 20 ppb, with slightly higher levels allowed in feeds. Because the level of aflatoxin in products destined for human consumption is strictly regulated in the U.S., aflatoxin contamination is primarily of economic importance. However, even though aflatoxin levels in foods is limited to 20 ppb, the effect of chronic exposure to low levels of aflatoxin on human health is unknown. Thus, some European countries require the presence of aflatoxin in foods intended for human consumption to be 0 ppb. In areas of the world where regulations do not exist, aflatoxin is a serious health problem (CAST, 1989).

Approaches to control of aflatoxin have been broadly grouped into preharvest and postharvest strategies. Proper grain storage can greatly reduce contamination postharvest, and some decontamination methods, while costly, are used, e.g., ammoniation. However, most research efforts at control of aflatoxin has been directed at the preharvest elimination of infection and contamination, since the ability to control preharvest contamination would reduce the need for postharvest elimination. Preharvest methods have included agricultural practices such as irrigation strategies designed to eliminate stress to crops associated with drought, which appears to increase production of aflatoxin by the fungus. Other methods include using regionally adapted varieties of crop plants. However, these methods have been expensive to implement and have not been completely effective. Chemical control methods have also been ineffective at controlling infection by these fungi.

The development of host plants that are resistant to *Aspergillus* infection and aflatoxin contamination has not been as successful as have programs for breeding resistance to other pathogens. In general, the resistant varieties that have been made are unstable from growing season to growing season and from region to region. Also, screening plants for resistance to colonization by *Aspergillus* spp. and aflatoxin contamination has been difficult. In corn, and frequently in cotton, inoculation methods have been difficult, often requiring wounding the plant to introduce the fungus, which may overwhelm the plants natural resistance reactions making it difficult to evaluate the plants resistance mechanisms (*Cotty, Plant Dis.* 73: 489–492 (1989)).

Methods have been developed for inhibiting mycotoxin production in crops. For example, U.S. Pat. No. 5,942,661 to Keller discloses a method of inhibiting mycotoxin production by introducing into the plant a gene encoding a lipoxygenase pathway enzyme of the mycotoxin. The method may produce transgenic plants that are substantially resistant to mycotoxin contamination. Mycotoxin resistance is further increased by introducing into the plant antisense genes for the 9-hyperoxide fatty acid producing lipoxygenases. However, reducing aflatoxin contamination by making transgenic plants resistant to aflatoxin production is expensive and time consuming, and since transformation efficiencies varies from plant species to plant species, the method may not be successful for all plant species. Furthermore, the long-term effect of introducing transgenic plants into the environment is unknown.

Since traditional methods for controlling fungal infection and/or production of aflatoxin by breeding, chemicals, or transgenic plants have not been completely effective, there is a need for an inexpensive and effective method for either controlling infection of crops by fungi such as *Aspergillus* spp. or *Gibberella* spp., or controlling the biosynthesis and accumulation of mycotoxins such as aflatoxin or deoxynivalenol in plants infected with fungi such as *Aspergillus* spp or *Gibberella* spp., respectively. There is also a need for a rapid and inexpensive method for identification of chemicals or compounds in natural extracts that inhibit production of mycotoxins such as aflatoxin and deoxynivalenol.

SUMMARY OF THE INVENTION

The present invention provides a substantially pure alkaloid compound that inhibits the biosynthesis of particular products of secondary metabolism. In particular, the present invention provides an alkenylene piperidine amide, which can be isolated from *Piper nigrum*. The alkenylene piperidine amide inhibits transcription from the nor-1 promoter, the tri5 promoter, ver-1 promoter, the verA promoter, the omt-1 promoter, the fas-1a promoter, alfR promoter, the ipna promoter, and mutant thereof. In a preferred embodiment the alkenylene piperidine amide inhibits at least transcription of the nor-1 promoter of *Aspergillus parasiticus*, the tri5 promoter of *Gibberella pulicaris* or the ver-1 promoter of *Aspergillus nidulans* without killing the fungus in vitro. In a preferred embodiment, the alkenylene is a C18 alkenylene with one or more double bonds. Preferably, the $C_{18}$ alkenylene has two to four double bonds.

The compound of the present invention is useful for inhibiting biosynthesis of a mycotoxin by a fungus growing on a plant material. In particular, the compound inhibits the biosynthesis of aflatoxin and deoxynivalenol. Thus, the present invention provides a formulation which comprises as an active ingredient an alkenylene piperidine amide wherein the alkenylene is a C18 alkenylene with one or more double bonds, or its salt, or its ester, associated with one or more acceptable carriers, excipients or vehicles therefore. Preferably, the C18 alkenylene has two to four double bonds.

Thus, the present invention provides the use of a compound, which is an alkenylene alkenylene piperidine amide, wherein the alkenylene is a C18 alkenylene with one or more double bonds for treatment of plant material to inhibit mycotoxin production by a fungus. Further, the present invention provides for use of the above compound for the preparation of a composition for treatment of a plant material to inhibit mycotoxin production by a fungus. In particular, wherein the plant material is selected from the group consisting of seeds, nuts, and animal feeds.

The present invention further provides a method for inhibiting mycotoxin biosynthesis by a fungus in a plant material comprising applying an effective amount of an alkenylene piperidine amide in a carrier to the plant material wherein the compound inhibits biosynthesis of the mycotoxin. In a preferred embodiment, the alkenylene is a C18 alkenylene with one or more double bonds, preferably, two to four double bonds. In the method, the alkenylene piperidine amide can be provided in the carrier at a concentration between about 1 and 100 $\mu$g/ml. In a preferred application, the plant material is selected from the group consisting of seeds, nuts, grains, and animal feeds.

Because the alkaloid of the present invention is able to inhibit the biosynthesis of mycotoxins, it would be useful to provide transgenic plants that are able to synthesize the alkaloid of the present invention. Therefore, the present invention further provides a transgenic plant that contains DNA comprising genes that encode enzymes involved in biosynthesis of the alkenylene piperidine amide wherein the compound synthesized by the transgenic plant inhibits biosynthesis of the mycotoxin by the fungus. In a preferred embodiment, transgenic plant produces an alkenylene piperidine amide wherein the alkenylene is a C18 alkenylene with one or more double bonds, preferably, two to four double bonds.

The present invention further provides a method for identifying compounds that inhibit biosynthesis of a product of secondary metabolism such as a mycotoxin in a fungus. In particular, a method is provided for identifying compounds that inhibit biosynthesis of aflatoxin by *Aspergillus* spp. and biosynthesis of deoxynivalenol by *Gibberella* spp.

Therefore, the present invention provides a method for determining whether a compound inhibits biosynthesis of a secondary metabolite comprising providing a culture of a transgenic fungus comprising a reporter gene operably linked to a promoter for a gene involved in the biosynthesis of the secondary metabolite, providing to the culture the compound to be determined, incubating the culture containing the extract under conditions that cause biosynthesis of the secondary metabolite, and measuring expression of the reporter gene wherein absence of expression of the reporter gene indicates that the compound inhibits biosynthesis of the secondary metabolite.

The present invention further provides a method for identifying and isolating a compound in a material that inhibits the biosynthesis of a secondary metabolite of a fungus comprising providing an extract of the material, separating the material into fractions or compounds by a chromatography method, providing a spore suspension of a transgenic fungus comprising a reporter gene operatively linked to a promoter that is the same as the promoter that controls transcription of a gene involved in biosynthesis of the secondary metabolite, adding the spore suspension to the separated compounds, allowing the spores to germinate and grow fungi, and detecting expression of the reporter gene wherein absence of expression of the reporter gene identifies the fractions or compounds that inhibits biosynthesis of the secondary metabolite. In a preferred embodiment of the method, the chromatography is thin layer chromatography (TLC) using TLC plates. Preferably, to grow the fungi the TLC plates are incubated in a dark moist atmosphere at 30° C. for a time sufficient for the fungi to cover the plate. It is further preferable that the fungi be lysed by freeze-thawing to release the reporter expression product.

In a preferred embodiment of the present invention, the secondary metabolite is a mycotoxin, preferably selected from the group consisting of aflatoxin, deoxynivalenol, or sterigmatocystin. In practicing the present invention, it is preferable that the transgenic fungus be a fungus selected from the group consisting of *Aspergillus parasiticus, Aspergillus nidulans, Aspergillus versicolor, Aspergillus flavus, Gibberella pulicaris*, and *Gibberella zeae*. In the present invention, it is preferable that the reporter gene be operably linked to a promoter that is selected from the group consisting of nor-1 promoter, ver-1 promoter, verA promoter, fas-1a promoter, omt-1 promoter, alfr promoter, ipna promoter, tri5 promoter, and mutant thereof. In an embodiment further still, it is preferable that the reporter gene be selected from the group consisting of a gene encoding β-glucuronidase, a gene encoding β-galactosidase, a gene encoding luciferase, and a gene encoding fluorescence green protein. In an embodiment further still, a transgenic fungus is provided that comprises a reporter gene operatively linked to a constitutive promoter, which provides a control for the method. Preferably, the constitutive promoter is the promoter for the bena gene or mutant thereof.

Therefore, it is an object to provide a compound that inhibits transcription of one or more genes encoding proteins involved in secondary metabolism of fungi. In particular, compounds that inhibit genes involved in biosynthesis of mycotoxins.

It is also an object of the present invention to provide a method for determining whether an extract comprises compounds that inhibit transcription of one or more genes encoding a protein involved in secondary metabolism of fungi. In particular, compounds that inhibit genes involved in biosynthesis of mycotoxins.

Further still, it is an object of the present invention to provide a method for identifying and purifying compounds that inhibit transcription of one or more genes encoding a protein involved in secondary metabolism of fungi. In particular, compounds that inhibit genes involved in biosynthesis of mycotoxins.

These and other objects of the present invention will become increasingly apparent with reference to the following drawings and preferred embodiments.

DESCRIPTION OF THE DRAWINGS

FIG. 8 shows the genomic DNA of SEQ ID NO:1, which encodes the nor-1 gene from *Aspergillus parasiticus*. (GenBank accession M27801). The gene spans nucleotides 269–1501 and the exons consists of nucleotides 269–317, 424–961, 1020–1119, and 1184–1258.

FIG. 9 shows the genomic DNA of SEQ ID NO:2, which encodes the ver-1 gene from *Aspergillus parasiticus* (GenBank accession M91369). The gene consists of nucleotides 396–1526 and the exons consist of nucleotides 496–822, 873–1196, and 1258–1395.

FIG. 10 shows the cDNA of SEQ ID NO: 3, which encodes the omt-1 gene from *Aspergillus parasiticus* (GenBank accession L22091). The coding region consists of nucleotides 12–1268.

FIG. 11 shows the genomic DNA of SEQ ID NO:5, which encodes the aflR gene from *Aspergillus parasiticus* (GenBank accession L26220). The gene consists of nucleotides 224–2379 and the coding region consists of nucleotides 418–1551.

FIG. 12 shows the genomic DNA of SEQ ID NO:6, which encodes the verA gene from *Emericella nidulans* (GenBank accession L27825). The gene spans *nucleotides* 555–1449 and consists of three exons, which span 555–887, 939–1262, and 1312–1449.

FIG. 13 shows the genomic DNA of SEQ ID NO:7, which encodes the Tri5 gene from *Gibberella pulicaris* (GenBank accession M64348). The gene spans nucleotides 401–1612 and consists of two exons, which span 401–869 and 930–1612.

FIG. 14 shows the genomic DNA of SEQ ID NO:8, which encodes the benA gene from *Aspergillus flavus* (GenBank accession M38265). The gene spans nucleotides 207–2121 and consists of eight exons, which span 207–218, 347–370, 440–466, 578–619, 701–754, 817–1607, 1672–2031, and 2085–2121.

DESCRIPTION OF PREFERRED EMBODIMENTS

Figure 1:
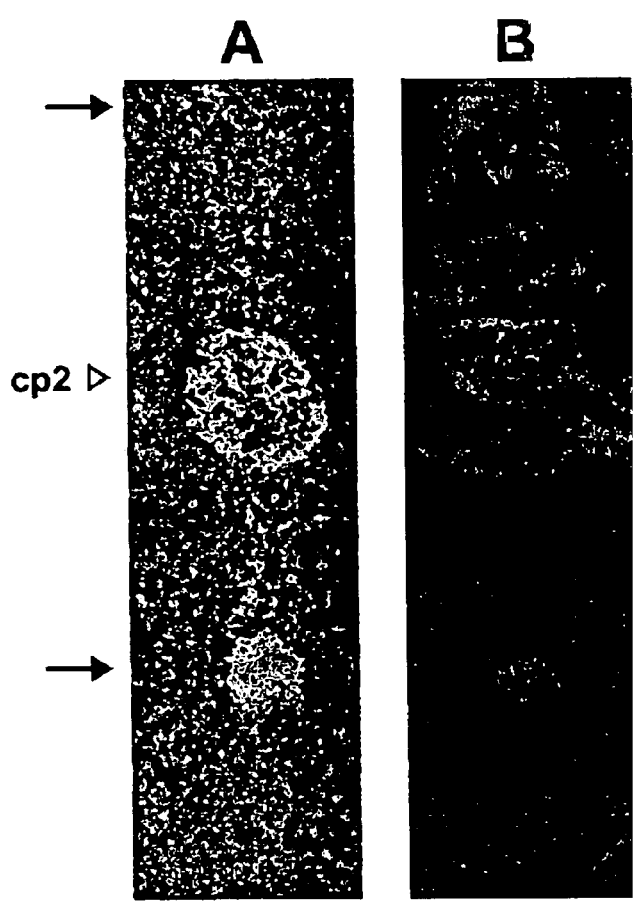
FIG. 1 shows a TLC plate with resolved crude pepper extract were coated with *Aspergillus parasiticus* G5 (nor-1-GUS fusion) in lane A or GAPN2 (benA-GUS fusion in lane B. Plates were subsequently coated with the GUS substrate X-gluc. The blue areas indicate GUS activity and the white areas indicate inhibition of GUS activity by the underlying resolved compounds. Fungal growth was seen in the area corresponding to compound Cp2. An unidentified fungitoxic compound inhibited fungal growth in both strains (arrow). The TLC solvent front is indicated by the arrowhead.

All patents, patent applications, and literature references cited in this specification are hereby incorporated herein by reference in their entirety. In case of conflict, the present description, including definitions, will control.

Provided herein is a method for determining whether a compound or an extract can inhibit biosynthesis of a secondary metabolite in a fungus. In particular, a method for identifying and purifying compounds that inhibit transcription of promoters that regulate transcription of genes encoding proteins, enzymes, or regulatory factors that are involved in biosynthesis of mycotoxins. As demonstrated herein the method is particularly useful for identifying and isolating compounds that inhibit biosynthesis of aflatoxin or deoxynivalenol. A novel aspect of the method is that it enables compounds that inhibit biosynthesis of mycotoxins to be distinguished and separated from compounds that inhibit growth of fungi.

The method disclosed herein enabled identification and isolation of an alkaloid from *Piper nigrum* (pepper), which is an alkenylene piperidine amide wherein the alkenylene group is a C18 alkenylene with two or more double bonds, that inhibits biosynthesis of aflatoxin and deoxynivalenol. In one embodiment, the alkaloid compound has the structure wherein the compound inhibits biosynthesis of a mycotoxin produced by a fungus. The position of the double bonds in any one of the species of the present invention is determined by the method of Cahoon et al., *Proc. Natl. Acad. Sci. USA* 89: 11184–11188 (1992).

The alkaoid of the present invention, designated Cp2, inhibits transcription from the nor-1 promoter, the ver-1 promoter, the tri5 promoter, and the ipnA promoter. These are all promoters for fungus genes that encode enzymes involved in biosynthesis of secondary metabolism products. The nor-1 and ver-1 genes encode enzymes involved in biosynthesis of aflatoxin, the tri5 gene encodes an enzyme involved in biosynthesis of deoxynivalenol, and ipnA encodes an enzyme involved in biosynthesis of penicillin. While Cp2 inhibits biosynthesis of the above secondary metabolites, Cp2 does not inhibit growth of the fungus in vitro. Thus, the inhibitory activity of Cp2 is distinguishable from piperine, which is also an alkaloid that is isolatable from *Piper nigrum*, because piperine inhibits fungus growth and transcription from the tri5 promoter but not transcription from the ipnA promoter.

Cp2 is useful as an inhibitor of mycotoxin biosynthesis by fungi and, therefore, is useful for preventing the contamination of plant material with mycotoxins. Cp2 is particularly useful for preventing contamination of the plant material with aflatoxin or deoxynivalenol. Plant material includes, but is not limited to, grains, nut products such as peanuts, or animal feeds. Cp2 can be isolated from pepper extracts or it can be produced by chemical synthesis. To prevent mycotoxin biosynthesis in a plant material contaminated with a fungus, Cp2 is admixed with the plant material in an amount sufficient to inhibit the contaminating fungus from producing its mycotoxin, in particular, inhibit the fungus from producing aflatoxin or deoxynivalenol. A carrier or solution comprising Cp2 can be used in a spray solution for treating the plant material, in dry admixture with a carrier that is ingestible, or in a wash solution for washing the plant material. The Cp2 concentration in the solution can be between about 1 and 100 µg/ml. In culture, Cp2 at a concentration of about 52 µg/ml or more was shown to completely inhibit transcription from the nor-1 promoter. Under particular conditions, the concentration of Cp2 in the solution can be less than 1 µg/ml. Treating the plant material with Cp2 enables the plant material to be stored for an extended period of time with reduced risk that the plant material will become contaminated with a mycotoxin. Thus, Cp2, which inhibits *Aspergillus* spp. and *Gibberella* spp. from producing aflatoxin and deoxynivalenol, respectively, when applied to the plant material, reduces the risk that stored plant material will be contaminated with aflatoxin or deoxynivalenol. Furthermore, it has been reported that in vivo mycotoxins perform an essential role in the ability of the fungus in invading and colonizing plant tissues. Thus, the present invention not only inhibits mycotoxin biosynthesis but can further prevent fungal growth on the plant material. The Cp2 is particularly useful inhibitor of mycotoxin and fungal growth in vivo because it inhibits transcription of several of the genes involved in mycotoxin biosynthesis simultaneously. The simultaneous inhibition of transcription of several genes indicates that fungi may be less able to mutate around the inhibitory effect of Cp2 than they would be in the case of an inhibitor directed against a single gene target. Thus, Cp2 can be used to prevent mycotoxin contamination of plant material with a reduced risk that fungus mutants would arise that are resistant to Cp2 than with mycotoxin inhibitors that are directed against a single gene or gene product.

The genes encoding the enzymes involved in Cp2 biosynthesis can be isolated and used to produce transgenic plants wherein the Cp2 is produced in the seed, nut, or grain of the plant for control of mycotoxin biosynthesis by fungi growing on the seeds, nuts, or grain. These genes can also be used to transform commercial strains of fungus to control the synthesis of undesirable secondary metabolites in pharmaceutical or food fermentations. These genes can also be used to transform bacteria to enable biosynthesis of Cp2 by commercial fermentation methods.

As demonstrated by the identification and isolation of Cp2, the present invention provides a bioassay for identifying extracts and particular compounds within the extract that inhibit the biosynthesis of mycotoxins that include, but are limited to, aflatoxin, sterigmatocystin, or deoxynivalenol. In a preferred embodiment, chromatography is used to separate the compounds in the extract, which are then tested as disclosed herein for the ability to inhibit a promoter for a gene involved in the biosynthesis of the mycotoxin. In particular, a promoter selected from the group consisting of the nor-1 promoter, the ver-1 promoter, the verA promoter, the fas-1a promoter, the omt-1 promoter, the alfR promoter, the ipnA promoter, and the tri5 promoter.

To determine whether an extract contains at least one compound that inhibits mycotoxin biosynthesis in a fungus, or to identify and purify the inhibitory compound, a transgenic fungus is provided, which comprises a reporter gene operably linked to a promoter to a gene involved in mycotoxin biosynthesis. The transgenic fungus is grown with the extract in a culture under conditions that stimulate biosynthesis of the mycotoxin. Optionally, the method provides that several cultures are provided, each containing a transgenic fungus with one of the aforementioned promoters operably linked to a reporter gene. It is preferable that a control culture is also provided, which contains the same transgenic fungus grown in the absence of the extract, and control cultures that contain a transgenic fungus comprising a reporter gene operably linked to a promoter involved in primary metabolism, grown in cultures both with the extract and without the extract. When an extract contains a compound that inhibits mycotoxin biosynthesis, transcription of the reporter gene is inhibited when the transgenic fungus is grown with the extract but is not inhibited when grown in the absence of the extract. In contrast, the control transgenic fungus containing the reporter gene operably linked to a primary metabolism promoter is not inhibited by the extract. Determination of whether transcription of the reporter gene is inhibited or not is accomplished by adding an indicator substrate that enables detection of reporter activity. Preferably, the fungi are lysed prior to addition of the indicator substrate. A suitable method for lysing the fungi is freeze-thawing to break down the cell membranes to allow the reporter to leak out of the fungi. Alternatively, the fungi can be harvested and protein extracts made by methods well known in the art, and the protein extracts tested for reporter activity.

To further identify and isolate a compound in an extract that inhibits a promoter controlling transcription of a gene involved in biosynthesis of a mycotoxin, the compounds of the extract are separated into compounds, components, or fractions by a method such as column or thin-layer chromatography (TLC) chromatography. Preferably, the chromatography method is thin layer chromatography and separation of the extracts into compounds, fractions, or components is accomplished using various developing solvents, which are well known in the art. The separated compounds, fractions., or components are incubated as above with the transgenic fungus comprising a reporter gene operably linked to a promoter involved in mycotoxin biosynthesis under conditions that stimulate biosynthesis of the mycotoxin. A control transgenic fungus comprising a reporter gene operably linked to a promoter involved in primary metabolism is also provided in a control incubation. Inhibition of transcription of the reporter gene controlled by the mycotoxin promoter but not the primary metabolism promoter indicates that the compound, fraction, or component inhibits mycotoxin biosynthesis in the fungus. Inhibition of reporter transcription is determined by detecting reporter activity using an indicator substrate. By using the above method or combining the above method with other purification methods well known in the art, the inhibitory compound can be purified. Alternatively, the extract is resolved into compounds, fractions, or components by TLC. The TLC plates are then completely coated with a spore solution of a transgenic fungi containing the reporter gene operably linked to a promoter involved in mycotoxin biosynthesis in a molten agarose solution. The agarose immobilizes the spores on the plate and when the fungi germinates from the spores the agarose prevents cross-contamination between particular areas of the plate. After allowing the agarose to solidify, the plates are incubated under conditions that promote fungus growth. When fungus growth becomes manifest, the fungi coated plates are treated to lyse the fungi, preferably by freeze-thawing the fungi. The TLC plates are then treated with an indicator substrate that enables determination of whether transcription of the reporter has been inhibited. Preferably, the indicator substrate is applied as a solution that contains molten agarose. The agarose, after it solidifies, immobilizes the indicator substrate to prevent cross-contamination.

In a preferred embodiment, the method screens for compounds that inhibit promoters involved in mycotoxin biosynthesis, which include, but are not limited to, promoters for genes encoding the following enzymes involved in the biosynthesis of aflatoxin: nor-1 (FIG. 8; SEQ ID NO:1) from *Aspergillus parasiticus* (Chang et al., *Curr. Genet.* 21: 231–233 (1992); Trail et al., *Appl. Environ. Microbiol.* 60: 4078–4085 (1994)), ver-1 (FIG. 9; SEQ ID NO:2) from *Aspergillus parasiticus* (Skory et al., *Appl. Environ. Microbiol.* 58: 3527–3537 (1992)), omt-1 (FIG. 10; SEQ ID NO:3) from *Aspergillus parasiticus* (Yu et al., *Appl. Environ. Microbiol.* 59: 3564–3571 (1993)), fas-1A (SEQ ID NO:4) from *Aspergillus parasiticus* (Mahanti et al., *Appl. Environ. Microbiol.* 62: 191–195 (1996)), alfR (FIG. 11; SEQ ID NO:5) from *Aspergillus parasiticus* (Chang et al., *Appl. Environ. Microbiol.* 59: 3273–3279 (1993); Payne et al., *Appl. Environ. Microbiol.* 59: 156–162 (1993)), verA (FIG. 12; SEQ ID NO:6) from *Emericella nidulans* (Keller et al., *Phytopathol.* 84: 483–488 (1994); or deoxynivalenol such as tri5 (FIG. 13; SEQ ID NO:7) from *Gibberella pulicaris* (Holn et al., *Molec. Plant-Microbe Interactions* 5: 249–256 (1992)). In a preferred embodiment, the transgenic fungus comprises a reporter gene that is operably linked to the nor-1 promoter, which is involved in the conversion of norsolorinic acid to averantin in the aflatoxin biosynthesis pathway, or the reporter gene is operably linked to the promoter for the tri5 gene, which is involved in the biosynthesis of deoxynivalenol. In addition, it is preferable that the method further include a control transgenic fungus comprising a reporter gene that is operatively linked to a promoter for a gene known not to be involved in secondary metabolism. An example of such a promoter is the promoter for the benA gene (FIG. 14; SEQ ID NO:8), which encodes β-tubulin in *Aspergillus flavus* (Woloshuk et al., *Appl. Environ. Microbiol.* 60: 670–676 (1994)). For any one of the above promoters and gene sequences, the present invention includes mutants thereof.

As used herein, the phrase "operably linked to a promoter" refers to both a recombinant nucleic acid molecule wherein the reporter gene is directly linked to the promoter with little or no nucleotides between the promoter and the reporter gene and to a recombinant nucleic acid molecule wherein the reporter gene is inserted into a gene controlled by the promoter in the proper codon reading frame to produce a chimeric or fusion polypeptide comprising the promoter's gene product with the reporter polypeptide inserted therein. The advantage of the latter is that it facilitates generation of transgenic fungi with the reporter gene inserted into the promoter's gene in the fungi by double crossover or homologous recombination. In general, when making plasmid constructs containing a reporter gene for use as vectors for making transgenic fungi by double crossover, it is preferable that a deletion be made in the coding region of the promoter's gene and replacing the reporter gene with the deleted material.

In particular embodiments, the fungi used to make the transgenic fungi include, but are not limited to, *Aspergillus* spp. such as *Aspergillus* parasiticus, *Aspergillus nidulans, Aspergillus versicolor, Aspergillus flavus*, and *Gibberella* ssp. such as *Gibberella zeae* and *Gibberella pulicaris*. Methods for DNA transformation of fungi have been taught by Skory et al. *Appl. Environ. Microbiol.* 56: 3315–3320 (1990); Oakley et al., *Gene* 61: 385–399 (1987); and, a method is taught herein. It is also envisioned that the above assays can be performed using bacteria transformed with the any one of the aforementioned promoters operably linked to a gene encoding a reporter.

In particular embodiments, the reporter gene that is operably linked to the secondary or primary metabolite promoter, includes but is not limited to, the uidA gene, which encodes β-glucuronidase (GUS); the lacZ gene, which encodes β-galactosidase; the luc gene, which encodes firefly luciferase; the rluc gene which encodes the *Renilla luciferase*; or the gene encoding the fluorescent green protein, which is disclosed in U.S. Pat. No. 5,958,713 to Thastrup et al. These reporter genes are commercially available and methods for their cloning and use are well known in the art. In the embodiment demonstrated herein, the reporter gene encodes the GUS enzyme. GUS was used as a reporter gene because GUS activity is easily monitored with a variety of indicator substrates including the histological stain, 5-bromo-4-chloro-3-indolyl-5-D-glucuronide (X-Gluc), which in the presence of the GUS enzyme is converted to a blue pigment, and 4-methylumbelliferyl-B-glucuronide (MUG), which in the presence of GUS can be converted to a fluorescent compound. These assays are well known in the art. The transgenic fungi herein comprise fungi wherein the GUS gene is operably linked to a promoter selected from the group consisting of the nor-1 promoter (isolatable from SEQ ID NO:1), the ver-1 promoter (isolatable from SEQ ID NO:2), the bena promoter (isolatable from SEQ ID NO:8), or the tri5 promoter (isolatable from SEQ ID NO:7) (Trail et al., *Proc. Am. Phytopathol. Soc. Nat. Mtg.*, Albuquerque, N. Mex. 1994; Payne et al., *Appl. Environ. Microbiol.* 59: 156–162 (1993)). The above sequences are particularly suitable for making transgenic fungi by double crossover or homologous recombination that produce the gene product and reporter as a chimeric or fusion polypeptide.

Examples of the GUS reporter gene operably linked to a promoter are shown in FIGS. 4A–4D which show DNA plasmid vectors pAPGUSN, pPAGUSNN, pHD6-6 (Wu et al., *Proc. Curr. Issues Food Safety, National Food Safety Toxicology Center*, Michigan State University, East Lansing, Mich.), and pGAP2 (Woloshuk et al., *Appl. Environ. Microbiol.* 60: 670–676 (1994)), respectively. The above plasmid vectors have been used to transform *Aspergillus parasiticus* strain NR1 (niaD–mutant from ATCC 5862, afl+, disclosed in Chang et al., *Curr. Genet.* 21: 231–233 (1992)), strain NR2, or strain C2N (Trail et al., *Appl. Environ. Microbiol.* 60: 4078–4085 (1994)). While strains NR1 and C2N were used to demonstrate practice of the present invention, other fungal strains, transformed with the plasmid vectors disclosed herein or plasmid vectors containing other promoters involved in biosynthesis of secondary metabolites operably linked to a gene encoding a reporter such as the GUS gene, can be used to detect inhibitors of secondary metabolites according to the present invention.

Plasmid pAPGUSN (FIG. 4A) contains the GUS gene operably linked to the nor-1 promoter at its 5' end and the nor-1 transcription terminator at its 3' end. pAPGUSN was stablely integrated into the genome of C2N, a nor-1, niaD+ strain, by double crossover insertion. In the same manner as above, a second plasmid, PAPGUSNN, comprising the nor-1 promoter operably linked to GUS and a functional niaD gene (FIG. 4B) was stablely integrated into strain NR1, which restored the niaD+phenotype to strain NR1, and preserved aflatoxin biosynthesis. A third plasmid similar to PAPGUSNN was made with the ver-1 gene promoter operably linked to the GUS gene (plasmid pHD6-6) (FIG. 4C) and used to transform *Aspergillus parasiticus*. In addition to the above transgenic fungi, a transgenic *Gibberella zeae* expressing GUS controlled by the tri5 gene promoter, a transgenic *Aspergillus nidulans* expressing GUS controlled by the ipnA promoter, and a transgenic *Aspergillus parasiticus* expressing GUS controlled by the benA promoter (plasmid pGAP2 in FIG. 4D) were also made in the same manner. The method for making plasmid FLIRT comprising the ipna promoter is disclosed by Bergh et al. in the *J. Bacteriol.* 178: 3908–3916 (1996). Methods for transforming fungi and recovering stable transformants are well known in the art. The aforementioned transgenic fungi can each be used in the present invention to identify and isolate compounds that inhibit biosynthesis of mycotoxins.

While particular plasmid vectors for making the transformed fungi are disclosed herein, transformed fungi equivalent to the transformed fungi disclosed herein can be made using any plasmid that contains the same or substantially the same sequences as disclosed by the particular plasmid vectors herein. Methods for isolating, cloning and manipulating DNA are well known in the are as are methods for producing transgenic fungi. Therefore, the DNA fragments comprising promoter and termination regions for any one of the mycotoxin biosynthesis genes can be isolated using in a polymerase chain reaction (PCR) appropriate primers to amplify the promoter and termination regions. Primers can be designed using methods well known in the arts. These amplified DNA fragments are then ligated to the 5' and 3' ends of a DNA encoding a reporter to form a cassette. DNA encoding reporters are commercially available. The cassette is inserted into any commercially available plasmid, which is linearized and used to transform any fungus, including those taught herein. Prior to transformation, additional genes such as the niaD gene can also be inserted into the plasmid. The novelty of the method resides in its ability to identify inhibitors of particular promoters controlling particular enzymes involved in mycotoxin biosynthesis and to distinguish the particular inhibitors from inhibitors that affect growth of the fungi, not in the particular transgenic fungi disclosed herein or the particular plasmids disclosed herein that were used to construct the transgenic fungi.

It is known that a wide variety of substances can inhibit aflatoxin biosynthesis; however, many of these substances also inhibit fungal growth, and often, the two processes have not been distinguished. However, unlike prior methods for identifying mycotoxin inhibitors, the present invention enables compounds that inhibit mycotoxin biosynthesis to be distinguished from compounds that inhibit both mycotoxin biosynthesis and primary metabolism. Hikoto et al. (*Mycopathologia* 66: 161–167 (1978)) reported that extracts of various condiments and herbal drugs inhibit mycotoxin biosynthesis. It is well known that pepper contains piperine, an alkaloid that inhibits fungus growth and therefor mycotoxin biosynthesis. However, using the method disclosed herein a novel compound in pepper extracts was identified that inhibits aflatoxin biosynthesis but not fungus growth in vitro. In particular, the method enabled the identification and isolation of compound Cp2, a novel alkaloid that inhibits the nor-1 promoter and thus, aflatoxin biosynthesis, but does not inhibit primary metabolism, since growth of the fungus was not inhibited in vitro. However, because mycotoxins have an important role in enabling fungi such as *Aspergillus* ssp. and

*Gibberella* ssp. to invade and colonize plant tissues, providing Cp2 to a plant material can effectively prevent the fungi from growing in the plant material.

Identification of Cp2 was by the following culture or batch and chromatography methods of the present invention. Transgenic fungus strain G5 containing the nor-1 promoter operably linked to the GUS reporter gene was grown in PMS medium, which does not support aflatoxin biosynthesis. After 72 hours, the transgenic fungus was transferred to GMS medium, which is an aflatoxin induction medium (Buchanan et al., *Appl. Environ. Microbiol.* 48: 306–310 (1984)). The above nutrient shift avoids differences in mycelial growth rates, which may occur between treatments. After the transfer to GMS medium, a chloroform extract of black pepper was added to medium. When GUS activity was measured, the pepper extract inhibited expression of GUS activity in transgenic strain G5 (FIG. 7) whereas a control culture of strain G5, to which no pepper extract was added, produced GUS activity (FIG. 7).

To show that the inhibition of GUS activity by the pepper extract was because of inhibition of the nor-1 promoter and not because some component of the pepper extract inhibited the GUS enzyme itself, the assay was repeated with transgenic fungus containing pGAP2, pAPGUSN (transformant G5), or pAPGUSNN. The pepper extract inhibited expression of GUS activity when GUS was under the control of the nor-1 promoter (pAPGUSN or pPAGUSNN), but not when GUS was under the control of the bena promoter (pGAP2). This indicated that the pepper extract did not inhibit the GUS enzyme by binding to the enzyme. Instead, inhibition was due to a component of the pepper extract, later identified as Cp2, interacting with the nor-1 promoter. The effect of black pepper extract on expression of GUS activity in *Aspergillus* transformed with the above vectors is shown in Table 1.

TABLE 1

| | GUS activity | |
|---|---|---|
| plasmid (promoter) | Pepper extract | No extract |
| pGAP2 (benA) | + | + |
| pAPGUSN (nor-1) | − | + |
| pAPGUSNN (nor-1) | − | + |

The method further enabled the novel Cp2 compound in the pepper extract that inhibited transcription of the nor-1 promoter, but not transcription of primary metabolism promoters, to be isolated. To isolate the Cp2 compound from the pepper extract, an aliquot of the pepper extract was resolved on silica plates by thin-layer chromatography (TLC). The TLC plates were then completely coated with a spore solution of transgenic fungus strain G5 containing about 0.3% molten agarose. After the agarose solidified, the plates were incubated under conditions that promoted growth of the transgenic fungus. Preferably, the plates were incubated at 30° C. for about two days in the dark. After fungus growth became manifest, the fungi covering the plates were lysed by freeze-thawing, preferably by freezing at −80° C. and thawing at room temperature. Next, the plates were covered with a solution of X-Gluc in about 0.6% molten agarose. The plates were then incubated 37° C. and monitored for β-glucuronidase activity. Blue areas signified that the hyphae in the area had β-glucuronidase activity whereas non-blue areas indicated the hyphae did not produce β-glucuronidase due to the presence of underlying inhibitory compounds. One area, designated Cp2, was subsequentlyshown to contain the novel Cp2 of the present invention. Control plates covered with a control fungus containing GUS under control of the bena promoter indicated that Cp2 did not inhibit fungus growth in vitro, only mycotoxin biosynthesis.

A preparative quantity of pepper extract was then resolved by flash column chromatography and column fractions were collected. The fractions were each analyzed by TLC as set forth above to identify those chromatography fractions that contained Cp2. The areas of the TLC plates corresponding to Cp2 were removed from the plate, pooled, concentrated, and re-chromatographed on TLC plates using a second solvent system to resolve the compounds. Optionally, the TLC purification method can be repeated until the compound is purified free of other compounds. After any purification step, an aliquot of the inhibitory material can be assayed on TLC plates or in the batch method to ensure that the material being purified retains the ability to inhibit mycotoxin biosynthesis. Purification of Cp2 required an additional TLC chromatography using a third solvent system which resulted in a Cp2 preparation of about 97% purity. As alternatives to TLC, column chromatography (e.g., ion exchange chromatography, size exclusion chromatography, HPLC, FPLC, etc.) or high voltage paper electrophoresis can be used to purify inhibitory compounds.

Cp2 was determined to inhibit transcription not only from the nor-1 promoter but also from the ver-1 promoter, the tri5 promoter, and the ipnA promoter. The inhibitory activity of Cp2 is distinguishable from piperine. Using the batch method of the present invention, piperine was unable to inhibit transcription from the ipnA promoter (FIG. 3A) even though it inhibited transcription from the tri5 promoter (FIG. 3B). Also, piperine inhibits fungus growth in vitro whereas Cp2 does not. Furthermore, Cp2 is distinguishable from other compounds that inhibit aflatoxin accumulation. For example, Huang et al. (*Phytopathol.* 87: 622–627 (1997)) identified from seeds of corn inbred for resistance to aflatoxin accumulation, a protein that inhibited aflatoxin accumulation by inhibiting growth of *Aspergillus flavus*, and another protein inhibited aflatoxin accumulation with little effect on fungal growth; Russin et al. (*Phytopathol.* 87: 529–533 (1997)) identified a component of unknown identity in the wax of kernels of corn bred to be resistant to *Aspergillus flavus* that is not present in the wax of corn kernels from corn not resistant to *Aspergillus flavus*; and Ghosh et al. (*J. Stored Products Res.* 32: 339–343 (1996)) identified three proteins in extracts of sorghum seeds that completely inhibited germination of *Aspergillus flavus* spores.

The following examples are intended to promote a further understanding of the present invention.

EXAMPLE 1

The method for identifying compounds that inhibit mycotoxin biosynthesis is illustrated using ground black pepper (Piper nigrum) extracts and assaying for compounds that inhibit aflatoxin biosynthesis.

Ground black pepper (500 mg) was extracted in 2L cyclohexanol overnight under a fume hood with constant stirring. After 24 hours, the mixture was filtered through Whatman paper and the extracted pepper filtrate was removed and in a similar manner to the above, extracted with chloroform followed by absolute ethanol. The filtrates from each extraction were concentrated by rotary evaporation and analyzed by thin layer chromatography (TLC).

The extracts were separated on TLC plates using a solvent system consisting of chloroform:acetone:toluene (25:40:35 v:v:v). Afterwards, the TLC plates were dried in a fume hood to evaporate any solvents left on the plates, and then placed silica-side down on a UV transilluminator and UV absorbent spots were traced on an acetate sheet. To identify compounds with aflatoxin inhibitory properties, a bioassay was invented that modified the screening method of Homans et al. (*J. Chromato.*, 51: 327–329 (1970)). The bioassay used two transgenic strains of *Aspergillus parasiticus*. The strain G5 had its nor-1 gene replaced by a DNA construct comprising the nor-1 promoter operably linked to GUS reporter gene (Xu et al. *Physiol. Molec. Plant Pathol.* 56: 185–196 (2000)). The strain GAPN2 had its niaD gene replaced by a DNA construct containing the β-tubulin bena promoter operably linked to the GUS reporter gene.

To perform the TLC bioassay, a spore solution of a transgenic *Aspergillus parasiticus* (strain G5) that contained the aflatoxin biosynthesis promoter nor-1 operably linked to the uidA gene, which encodes β-glucuronidase (GUS), was made at a final concentration of about $1 \times 10^6$ spores per ml in YES medium (a yeast extract and sucrose medium that induces aflatoxin biosynthesis in *Aspergillus* spp.) containing 0.3% agarose at 55 to 60° C. (20 ml will cover a plate that has a surface area of 200 $cm^2$). The spore solution was evenly sprayed across the TLC plate inclined at a 60° angle in a sterile hood using a glass TLC spray apparatus with care taken to ensure an even coating. After the agarose solidified, the plate was balanced on two glass test tubes on dampened paper towels in a moist chamber assembled from a plastic storage container with a loose lid that was completely lined with plastic wrap. Plates were incubated for 2 days at 30° C. in the dark. Following two days of growth, the plates were frozen for one hour at −80° C. and then thawed at room temperature for at least 30 minutes to break down the cell membranes of the fungi and allow the GUS enzyme to leak out of the fungi. Areas of inhibition of fungal growth were traced on acetate sheets for comparison to the UV absorbent spots. Then the plates were inclined at a 600 angle and sprayed using a TLC plate sprayer with a mixture of 15 ml. of 2×X-Gluc buffer (100 mM $KPO_4$, pH 7.0, 0.3% K ferricyanide, 0.1% X-Gluc (5-bromo-4-chloro-3-indolyl-β-D-glucuronide cyclohexylammonium salt (Gold Biotechnology, Inc., St. Louis, Mo.) added to 15 ml of 0.6% agarose at 55 to 60° C. immediately before spraying. The plates were wrapped in plastic film and incubated in a plastic storage container at 37° C. overnight. Areas that lacked β-glucuronidase activity were traced onto acetate sheets and compared to the locations for the UV absorbent spots and the areas that inhibited fungal growth.

Visual examination showed that the TLC plates were evenly covered with mycelia except for one area indicating that this area contained a compound that inhibited growth of the transgenic fungus (FIG. 1). GUS activity, which was indicated by a blue color, was not uniform over the entire surface of the TLC plate (FIG. 1, lane A). Additional area that lacked a blue color but had mycelial growth represented compounds that were inhibitory to the nor-1 promoter. Inhibition of GUS activity was not detected in a control consisting of a transgenic *Aspergillus parasiticus* containing plasmid pGAP2 comprising the GUS gene operatively linked to the promoter for the benA gene which encodes β-tubulin (FIG. 1, lane B). The control showed that the inhibitory effect of the compounds was not due to inhibition of GUS activity but was inhibition of GUS transcription via the nor-1 promoter. The area displaying inhibition of GUS transcription was chosen and the inhibitory compound was isolated.

This example shows that the present invention provides an easy and reliable TLC-based method to detect compounds inhibitory to transcription of secondary metabolism genes in *Aspergillus parasiticus*.

EXAMPLE 2

The following is a procedure for isolating Cp2 from ground pepper extracts.

Black ground pepper was suspended in cyclohexane (1:2 w:v) with constant stirring overnight. The mixture was filtered and then reextracted with cyclohexane for an additional four hours. The filtrates were combined and concentrated by rotary evaporation under vacuum at 40° C. After rotary evaporation, the cyclohexane extract was observed to have two phases. These phases were separated yielding a phase readily soluble in cyclohexane and a less dense phase readily soluble in ethanol. Both phases were tested to determine which phase contained the bioactive compound indicated in Example 1. An amount consisting of 10 $\mu$l of both phases were loaded onto separate TLC plates and the plates were developed using a solvent system consisting of chloroform:toluene:acetone (25:40:35 v:v:v). After development, the plates were dried overnight. Then the GUS bioassay was performed as shown in Example 1. The bioactive compound Cp2 was observed to be present in the ethanol soluble phase.

Flash chromatography was used to purify Cp2 from the pepper extract according to the method described by Still et al., *J. Org. Chem.* 43: 2923–2925 (1978). Flash chromatography uses an air pressure driven column which has been optimized for fast separations. The column used to purify Cp2 was dry packed with 6 inches of silica gel (grade 9385, 230–400 mesh, 60 angstrom available from Aldrich, Milwaukee, Wis.) between two layers of 50 mesh sand. Concentrated pepper extract filtrates made according to above were applied to the column and the column was then developed using a solvent system consisting of chloroform::toluene:acetone (25:40:6 v:v:v). Five ml aliquots were collected and analyzed on TLC plates to identify Cp2. The fractions containing Cp2 were pooled, concentrated by rotary evaporation, and resuspended in 100 proof ethanol and stored under refrigeration at 4° C. Approximately 10 mg of the concentrated fraction containing Cp2 was loaded onto a 20×20 cm preparatory TLC plate containing 1000 $\mu$m silica gel (60 angstrom, available from Whatman, Clinton, N.H.). The TLC plate was developed three times, each time using a solvent system consisting of hexane:acetone (2:1 v:v). After the third development, the TLC plate was dried and assayed for GUS inhibition as in Example 1. The bioactive band containing Cp2 was scraped out of the silica plate and eluted from the silica using chloroform:ethanol (4:1 v:v). The Cp2 product was then concentrated by gaseous hydrogen gas and loaded onto a TLC plate as above and developed three times, each time with a solvent system consisting of hexane:ethyl acetate (4:1 v:v) which provided sufficient separation to enable a single band containing Cp2 to be located. The Cp2 was recovered with a purity of approximately 97%. TLC bioassays as above were then used to confirm the inhibitory properties of the nearly homogenous preparation of Cp2. A preliminary structure of Cp2 was determined by mass spectrometry to comprise an unsaturated C18 fatty acid amide of piperidine.

Therefore, this example shows the isolation of the aflatoxin inhibitory compound of the present invention, Cp2, which had been identified by the method of the present invention demonstrated in Example 1.

EXAMPLE 3

Cp2 has a demonstrable effect on aflatoxin biosynthesis and nor-1 transcription. This example used *Aspergillus parasiticus* SU-1, a wild-type aflatoxin producing isolate, and consisted of analyzing aflatoxin biosynthesis by TLC and aflatoxin mRNA transcription by Northern analysis.

A nutritional shift protocol (Skory et al., *Appl. Environ. Microbiol.* 56: 3315–3320 (1990)) was used with the modifications below to determine the effect of Cp2 on expression of the nor-1 gene and aflatoxin biosynthesis. Six cultures of fungi were incubated in PMS (peptone mineral salts), a medium that does not induce biosynthesis of aflatoxin. After 48 hours, the mycelium from each culture were separately transferred to GMS (glucose mineral salts), a medium that induces biosynthesis of aflatoxin. At the same time Cp2 was added to five of the six cultures to provide cultures having a final concentration of 2.6 µg/ml, 26 µg/ml, 39 µg/ml, 52 µg/ml, and 78 µg/ml, respectively. Thirty-six hours later, a sample of each culture was removed for Northern analysis. Forty-eight hours later, the culture filtrate was analyzed by TLC for aflatoxin biosynthesis and RNA was extracted from the mycelium for Northern analysis. Direct competitive ELISA analyses were also performed to determine whether, for each sample, aflatoxin B1 (AFB1) was in the medium. The procedure was performed as described by Peska (*J. Assoc. Off. Anal. Chem.* 71: 1075–1081 (1988)) with anti-AFB1 antibodies and AFB1-horseradish peroxidase conjugate (both available by name from Michigan State University, East Lansing, Mich.).

Figure 2A:
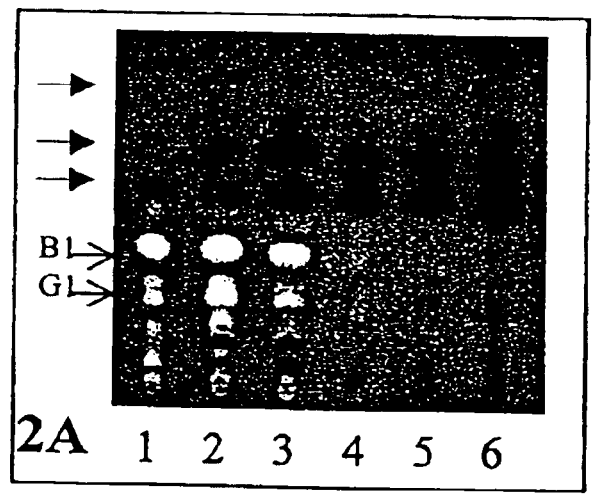
FIG. 2A shows the effect of various concentrations of Cp2 on aflatoxin biosynthesis in *Aspergillus parasiticus*. Samples were taken 48 hours after the addition of Cp2 to GMS medium containing the fungus and the aflatoxin components resolved on a TLC plate. The TLC plate was visualized under UV light. Lane 1, control; lane 2, extract from fungus grown in medium containing 2.6 $\mu$g/ml Cp2; lane 3, extract from fungus grown in medium containing 26 $\mu$g/ml Cp2; lane 4, extract from fungus grown in medium containing 39 $\mu$g/ml Cp2; lane 5, extract from fungus grown in medium containing 52 $\mu$g/ml Cp2; lane 6, extract from fungus grown in medium containing 78 $\mu$g/ml Cp2.
Figure 2B:
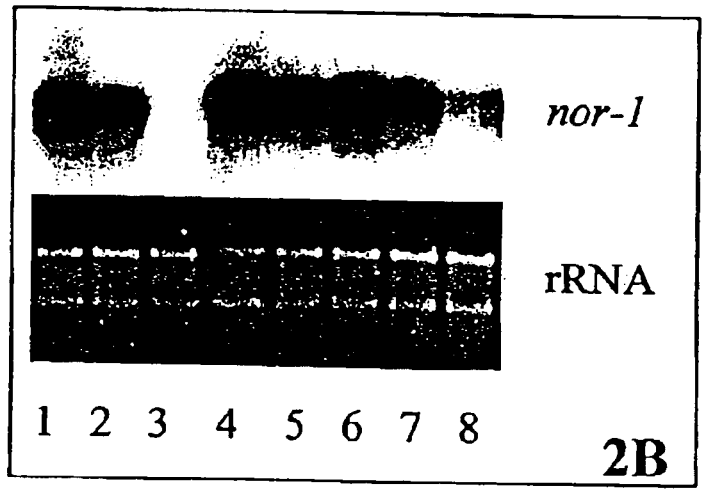
FIG. 2B shows the effect of various concentrations of Cp2 on accumulation of nor-1 transcripts in wild-type *Aspergillus* parasiticus SU-1. The lower panel is an agarose gel of RNA extracted from SU-1 grown at various concentrations of Cp2. The upper panel is a Northern analysis of the same gel probed with a labeled nucleotide probe to the nor-1 gene. Lanes 1–3 are samples analyzed 36 hours after Cp2 was added to the medium and lanes 4–8 are samples analyzed 48 hours after Cp2 was added to the medium. Lane 1, 36 hour control; lane 2, extract from fungus grown for 36 hours in medium containing 39 $\mu$g/ml Cp2; lane 3, extract from fungus grown for 36 hours in medium containing 52 $\mu$g/ml Cp2; Lane 4, 48 hour control; lane 5, extract from fungus grown for 48 hours in medium containing 2.6 $\mu$g/ml Cp2; lane 6, extract from fungus grown for 48 hours in medium containing 26 $\mu$g/ml Cp2; lane 7, extract from fungus grown for 48 hours in medium containing 52 $\mu$g/ml Cp2.

FIG. 2A shows Cp2 caused a reduction in the amounts of aflatoxins B1 and G1. FIG. 2A further shows that Cp2 at a concentration greater than 26 µg/ml appeared to completely inhibit biosynthesis of aflatoxin. Interestingly, Cp2 also caused an increase in the amount of an unidentified pigment that correlated with the decrease in aflatoxin. The significance of the increase in this pigment is unknown. FIG. 2B shows that Cp2 had an effect on the accumulation of nor-1 transcripts in the wild-type isolate SU-1. Samples had been collected 36 hours and 48 hours after adding the Cp2. FIG. 2B shows that Cp2 at a final concentration of 52 µg/ml appeared to completely inhibit nor-1 transcription within 36 hours after addition to the medium (lane 3). Lower concentrations of Cp2 did not completely inhibit nor-1 transcription (lanes 2, 5, 6 and 7).

This example demonstrates that Cp2 inhibits transcription of the nor-1 gene in *Aspergillus parasiticus* but does not inhibit growth of *Aspergillus parasiticus* itself.

EXAMPLE 4

The effect Cp2 and piperine on other secondary metabolite promoters is compared. For this comparison several transgenic fungi containing GUS operably linked to particular promoters involved in secondary metabolism pathways were used. A transgenic strain of *Aspergillus nidulans* (a penicillin producing fungus), FLIRT with the promoter for the ipnA gene (a gene involved in penicillin biosynthesis) operably linked to the GUS reporter gene, was provided by Dr. A. Brakhage, Technical University of DarmstAdt, Germany and a transgenic strain of *Gibberella zeae* with the promoter for the tri5 gene (a gene involved in deoxynivalenol biosynthesis) operably linked to the GUS reporter gene, was provided by Dr. N. Alexander, U.S. Department of Agriculture, Peoria, Ill.

Each transgenic fungus was grown in mycotoxin inducing liquid medium containing Cp2 or piperine. Aliquots were harvested from the cultures 48, 72, and 96 hours after the addition of either the Cp2 or piperine. Protein extracts were made from the harvested mycelia, and 10 µg/ml aliquots were tested for GUS activity. The substrate used to measure GUS activity was the fluorescence compound 4-methylumbelliferyl (MUG), which fluoresces under UV light.

Figure 3A:
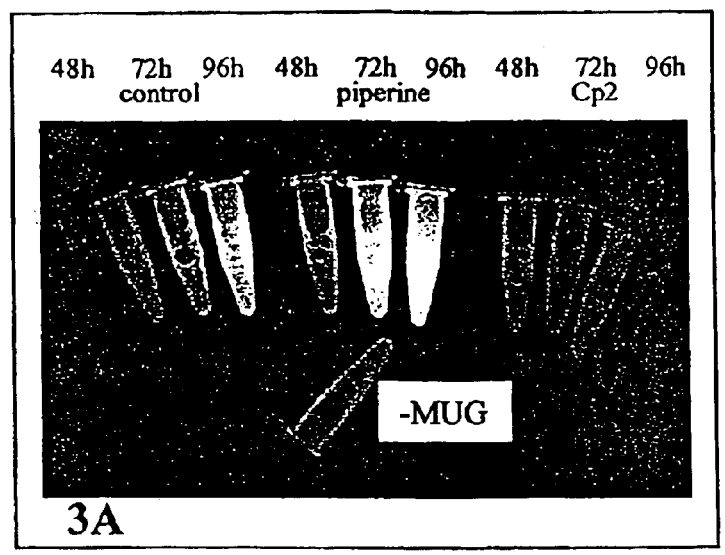
FIG. 3A shows the effect of Cp2 and piperine on the expression of GUS operably linked to the ipna promoter in a transgenic *Aspergillus nidulans* 48, 72, and 96 hours after addition to the medium. The GUS substrate was MUG (4-methylumbelliferyl glucuronide) and the samples were visualized using UV light.
Figure 3B:
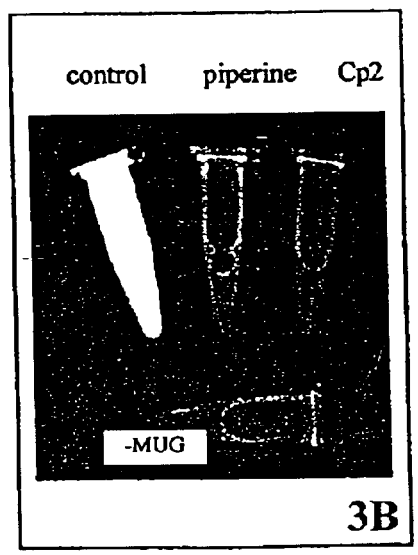
FIG. 3B shows the effect of Cp2 and piperine on expression of GUS operably linked to the tri5 promoter in a transgenic *Gibberella zeae* 96 hours after addition to the medium. The GUS substrate was MUG and the samples were visualized using UV light.

FIG. 3A shows that ipnA promoter in *Aspergillus nidulans* was inhibited by Cp2 but not by piperine whereas FIG. 3B shows that the tri5 promoter in *Gibberella zeae* was inhibited by both Cp2 and piperine.

The results in this example demonstrate that even though both Cp2 and piperine are obtainable from pepper, Cp2 and piperine are distinguishable compounds.

EXAMPLE 5

Construction of plasmid pAPGUSN having the GUS gene operably linked to the nor-1 promoter is illustrated. Standard molecular biology techniques were used to construct pAPGUSN.

Figure 4A:
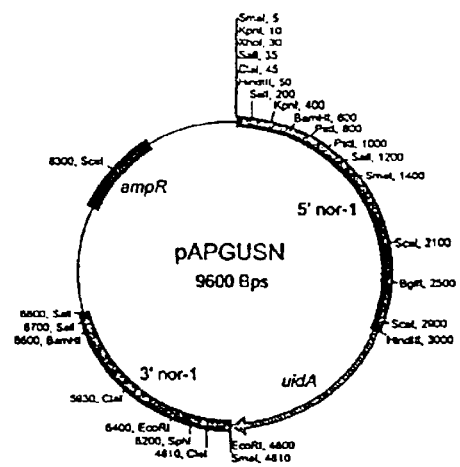
FIG. 4A shows a schematic diagram of a restriction enzyme map of plasmid PAPGUSN.
Figure 4B:
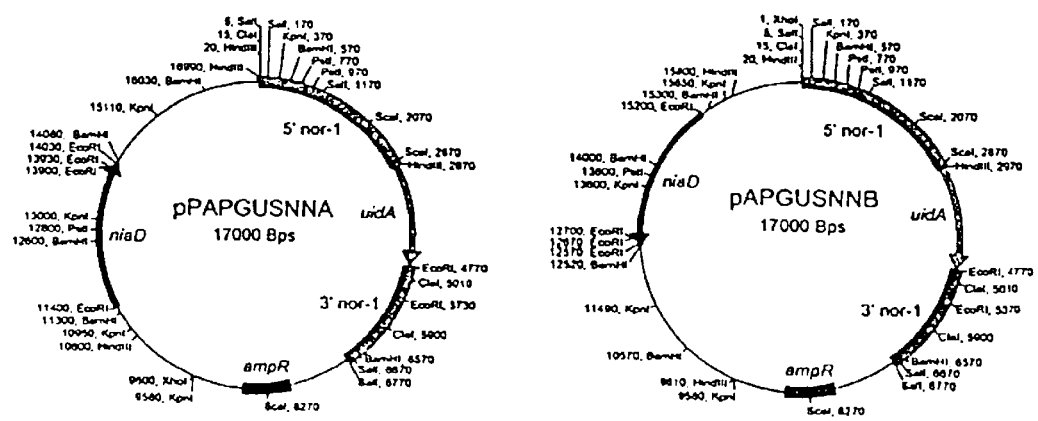
FIG. 4B shows a schematic diagram of a restriction enzyme map of plasmid pAPGUSNN. Plasmid pPAPGUSNNA contains the niaD gene in a clockwise orientation, and PAPGUSSNB contains the niaD gene in a counter-clockwise orientation.
Figure 4C:
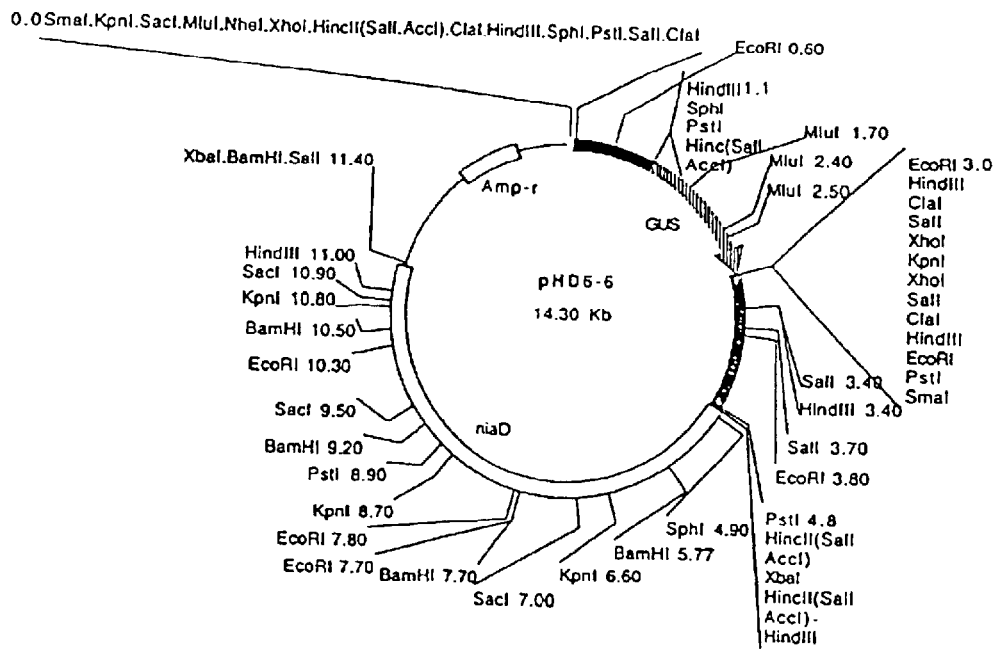
FIG. 4C shows a schematic diagram of a restriction enzyme map of plasmid pHD6-6.
Figure 4D:
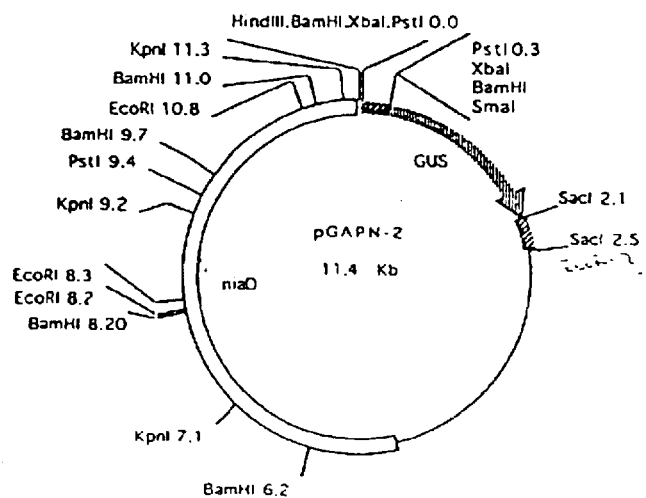
FIG. 4D shows a schematic diagram of a restriction enzyme map of plasmid pGAP2.

A 3.1 kb HindIII-Bsu361 DNA fragment from the nor-1 gene (sequence available from Trail et al., *Appl. Environ. Microbiol.* 60: 4078–4085 (1994) that included the translational start site and 64 nucleotides 3' of the translational start site was blunt-end ligated to a 5' NcoI site of a DNA encoding uidA (GUS reporter gene) using a 10 bp HindIII DNA linker (available from New England Biolabs, Beverly, Mass.) to maintain integrity of the reading frame. To form the translational termination sequence, a 2.0 kb BstY1 DNA fragment from the nor-1 3' untranslated region, including 18 bp upstream of the translational termination site, was ligated to the BamHI site at the 3' end of the GUS gene. The ligated product inserted into an ampicillin resistant plasmid to generate plasmid vector pAPGUSN. The plasmid vector was sequenced at the 5' junction of the nor-1-GUS fusion to confirm that the correct reading frame was preserved using primers for the promoter and for the GUS gene for double-stranded DNA sequencing. Sequencing was performed using a Sequenase chain-termination sequencing kit (available United States Biochemical Corp., Cleveland, Ohio) according to the manufacturer's instructions. FIG. 4A shows the plasmid map for pAPGUSN.

EXAMPLE 6

*Aspergillus parasiticus* C2N is transformed with PAPGUSN to illustrate construction of transgenic fungi that express GUS under the control of a secondary metabolism promoter.

*Aspergillus parasiticus* C2N is a nor-1 disrupted transformant that accumulates the aflatoxin precursor, norsolorinic acid (NA). C2N was derived from NR-1, which is a nitrate reductase-deficient aflatoxin producing isolate, derived from wild-type *Aspergillus parasiticus* SU-1 (available as NRRL 5862) by spontaneous mutation to chlorate resistance (Horng et al., *Molec. Gen. Genet.* 224: 294–296 (1990)), by inserting the nitrate reductase gene, niaD, into the nor-1 gene as described in Trail et al. (*Appl. Environ. Microbiol.* 60: 4078–4085 (1994)). C2N strains accumulate the orange-pigmented aflatoxin precursor norsolinic acid and makes reduced amounts of aflatoxin due to bifurcation in the aflatoxin biosynthesis pathway. Even though the aflatoxin produced by strain C2N is reduced in comparison to strain SU-1, the timing of aflatoxin biosynthesis is similar. Double recombination between the nor-1 flanking regions of pAPGUSN and the nor-1 flanking regions on the chromosome results in the replacement of the disrupted nor-1 in C2N with the nor-1-GUS fusion, resulting in a norsolorinic acid-accumulating, niaD–, GUS+ transformant. This causes the loss of a functional niaD gene present in the disrupted nor-1 gene of C2N, thus rendering the GUS expressing transformants to niaD–.

To make the transgenic *Aspergillus parasiticus* C2N, the plasmid pAPGUSN was linearized with Kpn1 before transformation. Polyethylene glycol-mediated transformation was carried out as described in Oakley et al., *Gene* 61: 385–399 (1987)) with modifications as disclosed in Skory et al. (*Appl. Environ. Microbiol.* 56: 3315–3320 (1990)).

Therefore, to perform the fungal transformations, $1 \times 10^8$ conidia were inoculated into a 250 ml Erlenmeyer flask containing 100 ml Czapek-Dox (CZ) medium (Difco) supplemented with 1% peptone or YES medium. Prior to transformation the flask was coated with a silanizing agent such as PROSIL, or dichlorodimethylsilane to prevent the mycelium from adhering to the glass and growing at the air interface. The culture was grown overnight at 29° C. in an orbital shaker (about 16–18 hours). Growth was visibly evident, but not excessive. Ideally, microscopic examination revealed that the majority of the conidia had formed germ tubes which were beginning to branch. The mycelial growth was harvested using a sterile Buchner funnel containing a MIRA-CLOTH filter and washed with water to remove spores. Then, the collected cells were transferred to a sterile 250 ml flask and resuspended in 40 CZ medium. To make protoplasts, 40 ml of digestion solution (filter sterilized 5 mg/ml Novozyme-234 in 1.1 M KCL, 0.1 M citrate, pH 5.8) was added. The cells were incubated for 3 hours at 30° C. with gentle shaking. Afterwards, the cells were filtered by gravity through a 29 Um nylon mesh weave filter and the protoplasts harvested at 5,000 rpm in a Sorval SS34 rotor (3,000×g) for 15 minutes at 4° C. The following operations were performed on ice. Next, the protoplasts were resuspended in 1 ml PEG buffer (0.6 M KCL, 0.05 M $CaCl_2$, 1 mM Tris-HCl, pH 7.5) and pelleted in a microcentrifuge at 4,500×g for 1 minute. This washing process was repeated three times. Afterwards, the washed protoplasts were resuspended in no more than 500 µl PEG-buffer and distributed in 100 µl aliquots for transformation. Five µl DNase inhibitor aurentricaboxylic acid (20 mM aurentricarboxylic acid, mM Tris-HC1, pH 7.0) was added and mixed gently. Then, 1–10 µg of plasmid DNA was dissolved in a volume of less than 10 µl and added followed by addition of 50 µl of freshly prepared and filter sterilized PEG solution (25% polyethylene glycol 3350, 0.6 M KCL, 0.05 M $CaCl_2$, 10 mM Tris-HCl, pH 7.5). The transformation mixture was gently mixed and incubated on ice for 20 minutes. Then, 850 µl PEG solution was gently added and the mixture allowed to sit at room temperature for 30 minutes.

After the transformation reaction, nitrate non-utilizing transformants (niaD−, GUS+) of strain C2N were selected on CZ medium amended with 58 g/L potassium chlorate, 100 g/L glutamate, and 20% sucrose (CCGS medium). Coconut agar medium (CAM; made according to Arseculeratne et al. (*Appl. Microbiol.* 18: 88–94 (1969)), an aflatoxin inducing medium, was used to screen the transformants for changes in accumulation of aflatoxin or precursors according to Davis et al. (*Microbiol.* 53: 1593–1595 (1987)).

In two transformation experiments, six of the eight transformants recovered from the CCGS selection medium produced GUS activity as measured by a MUG assay. Southern analysis confirmed the presence of a single nor-1-GUS fusion genes at the site of nor-1 and the accompanying loss of the niaD gene from that region. Three of the GUS expressing transformants had unexpected rearrangements present in their DNA at the nor-1 region and were eliminated from further analysis. Unexpectedly, replacement of the disrupted nor-1 gene with the nor-1-GUS fusion resulted in the loss or NA accumulation in all cases, although aflatoxin B1 continued to be produced as expected. Further analysis by Southern hybridization did not reveal any explanation for the loss of pigment production, although small rearrangements of nucleotides in the region of insertion that might affect expression would not have been detected by Southern hybridizations. Among the three remaining transformants, transformant G5 produced the highest amount of GUS activity in culture and was chosen for further study.

EXAMPLE 7

Transformants made in Example 5 were analyzed for their growth, aflatoxin biosynthesis, and GUS activity in culture.

Flasks containing 100 ml of YES broth and 5 glass beads to keep the mycelia dispersed, were inoculated with $1.75 \times 10^7$ spores each. The cultures were grown in an orbital shaker at 175 rpm at 28° C. Mycelia was harvested 16, 24, 36, 48, and 72 hours after inoculation. Dry weights were determined by drying the mycelial mats overnight at 60° C. GUS activity assays were performed on 10 mg total protein from ground tissue extracts using the GUS substrate MUG as described in Liang et al., *Appl. Environ. Microbiol.* 63: 1058–1065 (1997). GUS activity was determined using a spectrofluorometer with an excitation wavelength of 365 nm and an emission wavelength of 455 nm. Protein content of the supernatant was determined by a BCA assay (available from Sigma Chemicals, St. Louis, Mo.). Direct competitive ELISA analyses were performed on samples of the culture medium to determine concentrations of aflatoxin B1. The procedures performed as described in Peska (*J. Assoc. Off. Anal. Chem.* 71: 1075–1081 (1988)) with aflatoxin B1 monoclonal antibodies and aflatoxin B1-horseradish peroxidase conjugate.

The results show that there was a similar temporal pattern of aflatoxin B1 biosynthesis between paternal isolate C2N and G5 with lower levels of biosynthesis by G5 (FIG. 8). Biosynthesis of aflatoxin B1 in NR1 (niaD parent of C2N) exhibited a similar temporal pattern but, as expected, reached a higher quantity, 42.5 µg/ml culture medium after 72 hours. Comparison of GUS expression by G5 and C2N showed that mycelial extracts of G5 had increased GUS activity for up to 72 hours and no GUS expression was detected in mycelial extracts of C2N (FIG. 9). Dry weights were not significantly different among all cultures at each time point.

EXAMPLE 8

The transgenic fungi were also evaluated for its ability to colonize peanut plants.

The transgenic fungus was introduced onto peanut plants and the peanut plants were cultivated under drought conditions. About 6–8 weeks after introduction, the peanuts were harvested and the harvested pods underwent treatment for GUS expression. The kernels were split and the halves were cut perpendicular to their longitudinal axis into pieces approximately 4 to 5 mm wide. To follow the path of infection of the fungus through the peanut, the correct orientation of the shell, integument, and kernel was maintained during fixation and embedding. This was accomplished by threading a nylon strand through the center of each peanut piece, penetrating the shell, integument, and kernel sequentially. The threaded pieces were prepared for cytological study by briefly fixing with 5% formaldehyde in 50 mM potassium phosphate, pH 7.0 for 5–30 minutes on ice under a vacuum. This preliminary fixation killed the fungus while not affecting GUS activity. After rinsing in sterile distilled water, the peanut parts were incubated overnight with X-Gluc in 50 mM potassium phosphate, pH 7.0, containing 0.5 mM potassium fericyanide and 10 mM EDTA for detection of GUS activity. Following a brief rinse in water, the stained tissues were transferred to a solution of 3.7% formaldehyde, 5% acetic acid, 47.5% ethanol for at least 24 hours. Then, the tissues were dehydrated through a tert-butanol series and embedded in paraffin (PARAPLAST PLUS available from Fisher Scientific, Inc., New Brunswick, N.J.). During the final embedding step, the nylon thread was removed and the peanut pieces were aligned to allow sectioning through all three tissues perpendicular to the original long axis of the peanut. Paraffin blocks were sectioned at 12–15 mm, and serial sections were placed on glass slides coated with Haupt's solution. Following dewaxing of the sections with xylene and rehydration through an ethanol series, some of the sections were stained with 0.2% Chlorazol Black. The sections were mounted in Permount. Microscopy was carried out on a Ziess Axioskop equipped with DIC optics or an Olympus Vanox-S microscope with phase contrast optics.

Figure 5A:
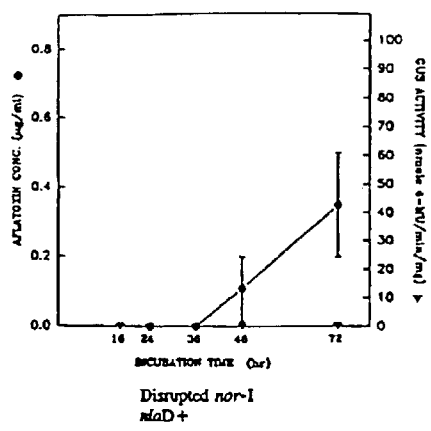
FIG. 5A shows time course assays on the expression of aflatoxin biosynthesis and GUS activity in parental *Aspergillus parasiticus* strain C2N.
Figure 5B:
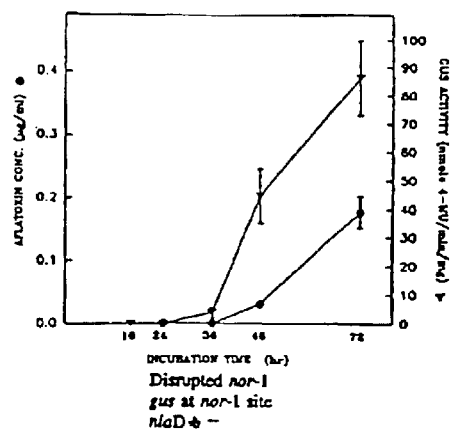
FIG. 5B shows time course assays on the expression of aflatoxin biosynthesis and GUS activity in strain G5 containing plasmid pAPGUSN.
Figure 6:
FIG. 6 shows GUS expression under the control of the nor-1 promoter in mycelia growing in peanut testa. *Aspergillus parasiticus* C2N was the fungal strain transformed with pAPGUSN, and the peanut pods comprising the testa were stained with X-Gluc.
Figures 7A, 7B:
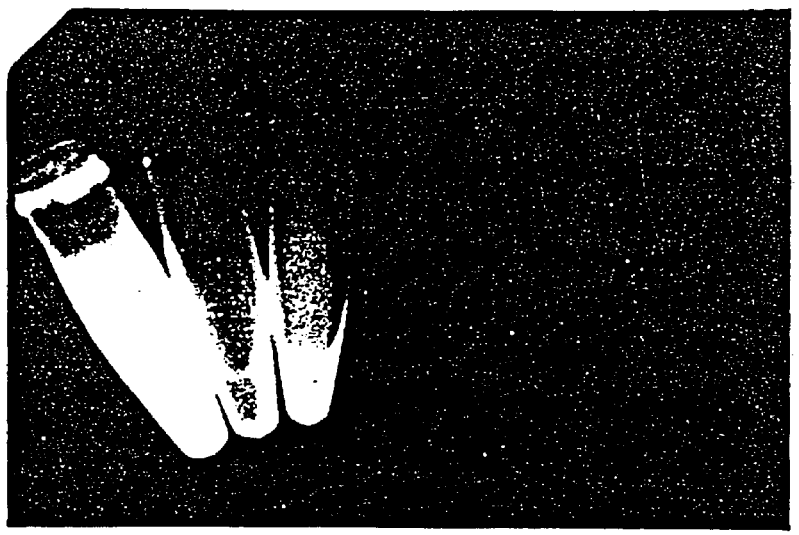
FIG. 7A shows transformed fungus strain G5 (containing pAPGUSN) grown without the addition of a pepper extract. Mycelia were harvested, macerated, and extracts were used to detect GUS activity using the GUS substrate MUG. The photograph was taken under UV illumination. Shown are three independent experiments without the pepper extract.
FIG. 7B shows transformed fungus strain G5 grown with the addition of a pepper extract. Mycelia were harvested, macerated, and extracts were used to detect GUS activity using the GUS substrate MUG. The photograph was taken under UV illumination. Shown are three independent experiments with the pepper extract.

When the peanuts were stained for GUS using the substrate X-Gluc, the fungus was clearly visible in the infected kernels. However, the blue color associated with GUS activity was not observed in conidia, conidiophores, nor the external mycelia surrounding the pod. This was expected because aflatoxin precursors do not accumulate in conidia and conidiophores (Keller at al., *Phytopathol.* 84: 483–488 (1994)). FIG. 5 shows that the production of GUS activity in the transgenic fungus was similar in time course to aflatoxin biosynthesis. These results indicate that the nor-1 promoter was functioning in the transgenic fungus in the same manner as it functions in the wild-type fungus.

A transformant of *Aspergillus parasiticus* strain NR2, strain 664, was made, which contained the GUS reporter gene under the control of the ver-1 promoter integrated into the ver-1 gene without disrupting normal aflatoxin biosynthesis (Liang et al., ibid). Strains NR1 and NR2 are independent spore isolates of the same spontaneous mutant of chlorate resistance.

Transgenic strains G5 and 664 can be used as in the bioassay of the present invention to detect and identify compounds that inhibit the biosynthesis of aflatoxin.

While the present invention is described herein with reference to illustrated embodiments, it should be understood that the invention is not limited hereto. Those having ordinary skill in the art and access to the teachings herein will recognize additional modifications and embodiments within the scope thereof. Therefore, the present invention is limited only by the Claims attached herein.

What is claimed is:

1. A substantially pure compound isolated from *Piper nigrum* consisting essentially an alkenylene piperidine amide wherein the alkenylene is a C18 alkenylene with four double bonds.

2. A formulation which consists essentially of as an active ingredient an alkenylene piperidine amide isolated from *Piper nigrum* wherein the alkenyl is a C18 alkenylene with four double bonds, or its salt, or its ester, and one or more acceptable carriers, excipients or vehicles therefor for use in inhibiting mycotoxin biosynthesis in fungi.

* * * * *

UNITED STATES PATENT AND TRADEMARK OFFICE
CERTIFICATE OF CORRECTION

PATENT NO. : 6,825,216 B1
DATED : November 30, 2004
INVENTOR(S) : Frances Trail, Raymond Hammerschmidt and John E. Linz It is certified that error appears in the above-identified patent and that said Letters Patent is hereby corrected as shown below:

Title page, Item [54] and Column 1, lines 1-4,
Title, "ALKALOID THAT INHIBITS BIOSYNTHESIS OF MICROTOXINS AND METHODS FOR SCREENING FOR MYCOTOXIN INHIBITORS" should be
-- ALKALOID THAT INHIBITS BIOSYNTHESIS OF MYCOTOXINS AND METHOD FOR SCREENING FOR MYCOTOXIN INHIBITORS --.

Column 1,
Lines 23 and 24, "wherein the alkenylene alkenylene with" should be -- wherein the alkenylene is a C18 alkenylene with --.

Column 3,
Line 19, "ipna" should be -- ipnA --.
Line 26 and 27, "the $C_{18}$ alkenylene" should be -- the C18 alkenylene --.
Line 40, "alkenylene alkenylene piperidine" should be -- alkenylene piperidine --.

Column 4,
Line 57, "ipna promoter" should be -- ipnA promoter --.
Line 66, "bena gene" should be -- benA gene --.

Column 5,
Line 63, "the ipna promoter" should be -- the ipnA promoter --.

Column 6,
Line 7, "plasmid PAPGUSN" should be -- plasmid pAPGUSN --.
Line 11, "and PAPGUSSNB" should be -- and pAPGUSSNB --.

Column 7,
Line 49, "The alkaoid of" should be -- The alkaloid of --.

Column 11,
Line 14, "the rluc gene" should be -- the Rluc gene --.
Line 23, "indolyl-5-D-glucuronide" should be -- indolyl-β-D-glucuronide --.
Line 32, "the bena" should be -- the benA --.
Line 65, "PAPGUSNN" should be -- pAPGUSNN --.

Column 12,
Line 3, "PAPGUSNN" should be -- pAPGUSNN --.
Line 13, "the ipna" should be -- the ipnA --.
Line 25, "the are as are methods" should be -- the art as are methods --.

UNITED STATES PATENT AND TRADEMARK OFFICE
CERTIFICATE OF CORRECTION

PATENT NO. : 6,825,216 B1
DATED : November 30, 2004
INVENTOR(S) : Frances Trail, Raymond Hammerschmidt and John E. Linz It is certified that error appears in the above-identified patent and that said Letters Patent is hereby corrected as shown below:

Column 13,
Line 27, "the bena" should be -- the benA --.

Column 14,
Line 1, "the bena" should be -- the benA --.

Column 15,
Line 10, "bena promoter" should be -- benA promoter --.
Line 34, "at a 600 angle" should be -- at a 60° angle --.

Column 18,
Lines 39 and 40, "PAPGUSN" should be -- pAPGUSN --.

Column 19,
Line 25, "29 Um nylon" should be -- 29 µm nylon --.
Line 29, "$CaCl_{21}$ mM" should be -- $CaCl_2$, 10mM --.
Lines 35 and 36, "acid, mM" should be -- acid, 5 mM --.

Signed and Sealed this

Sixteenth Day of May, 2006

JON W. DUDAS
*Director of the United States Patent and Trademark Office*